United States Patent [19]

Sikkenga et al.

[11] Patent Number: 5,401,892

[45] Date of Patent: * Mar. 28, 1995

[54] PREPARATION OF A DIMETHYLTETRALIN BY CYCLIZING AN ORTHOTOLYLPENTENE PHENYLHEXENE USING AN ULTRA-STABLE CRYSTALLINE ALUMINOSILICATE MOLECULAR SIEVE Y-ZEOLITE

[75] Inventors: David L. Sikkenga; Ian C. Zaenger, both of Wheaton, Ill.; Joyce D. Lamb, Ringgold, Ga.; Gregory S. Williams, Tampa, Fla.

[73] Assignee: Amoco Corporation, Chicago, Ill.

[ * ] Notice: The portion of the term of this patent subsequent to Aug. 21, 2007 has been disclaimed.

[21] Appl. No.: 24,152

[22] Filed: Feb. 26, 1993

Related U.S. Application Data

[63] Continuation of Ser. No. 794,018, Nov. 19, 1991, abandoned, which is a continuation of Ser. No. 633,068, Dec. 21, 1990, abandoned, which is a continuation-in-part of Ser. No. 539,007, Jun. 15, 1990, Pat. No. 5,030,781, and a continuation-in-part of Ser. No. 539,087, Jun. 15, 1990, Pat. No. 5,034,561, and a continuation-in-part of Ser. No. 556,297, Jul. 20, 1990, Pat. No. 5,073,670, which is a continuation-in-part of Ser. No. 316,308, Feb. 27, 1989, Pat. No. 4,950,825, which is a continuation-in-part of Ser. No. 211,000, Jun. 24, 1988, abandoned.

[51] Int. Cl.$^6$ .................................................. C07C 15/24
[52] U.S. Cl. ................................. 585/320; 585/410; 585/411; 585/430; 585/477; 585/480; 585/481
[58] Field of Search ............... 585/410, 411, 320, 400, 585/430, 477, 480, 481

[56] References Cited

U.S. PATENT DOCUMENTS

| | | | |
|---|---|---|---|
| 4,950,825 | 8/1990 | Sikkenga et al. | 585/320 |
| 5,030,781 | 7/1991 | Sikkenga et al. | 585/320 |
| 5,034,561 | 7/1991 | Sikkenga et al. | 585/320 |

FOREIGN PATENT DOCUMENTS 4896577 10/1993 Japan.

*Primary Examiner*—Asok Pal
*Attorney, Agent, or Firm*—Thomas E. Nemo; Wallace L. Oliver

[57] ABSTRACT

A method for preparing one or more specific dimethyltetralins from either 5-(o-, m-, or p-tolyl)-pent-1- or -2-ene or 5-phenyl-hex-1- or -2-ene, and optionally for preparing one or more specific dimethylnaphthalenes from the aforesaid dimethyltetralins is disclosed wherein the orthotolylpentene or phenylhexane is cyclized to the dimethyltetralin using an ultra-stable crystalline aluminosilicate molecular sieve Y-zeolite.

28 Claims, 1 Drawing Sheet

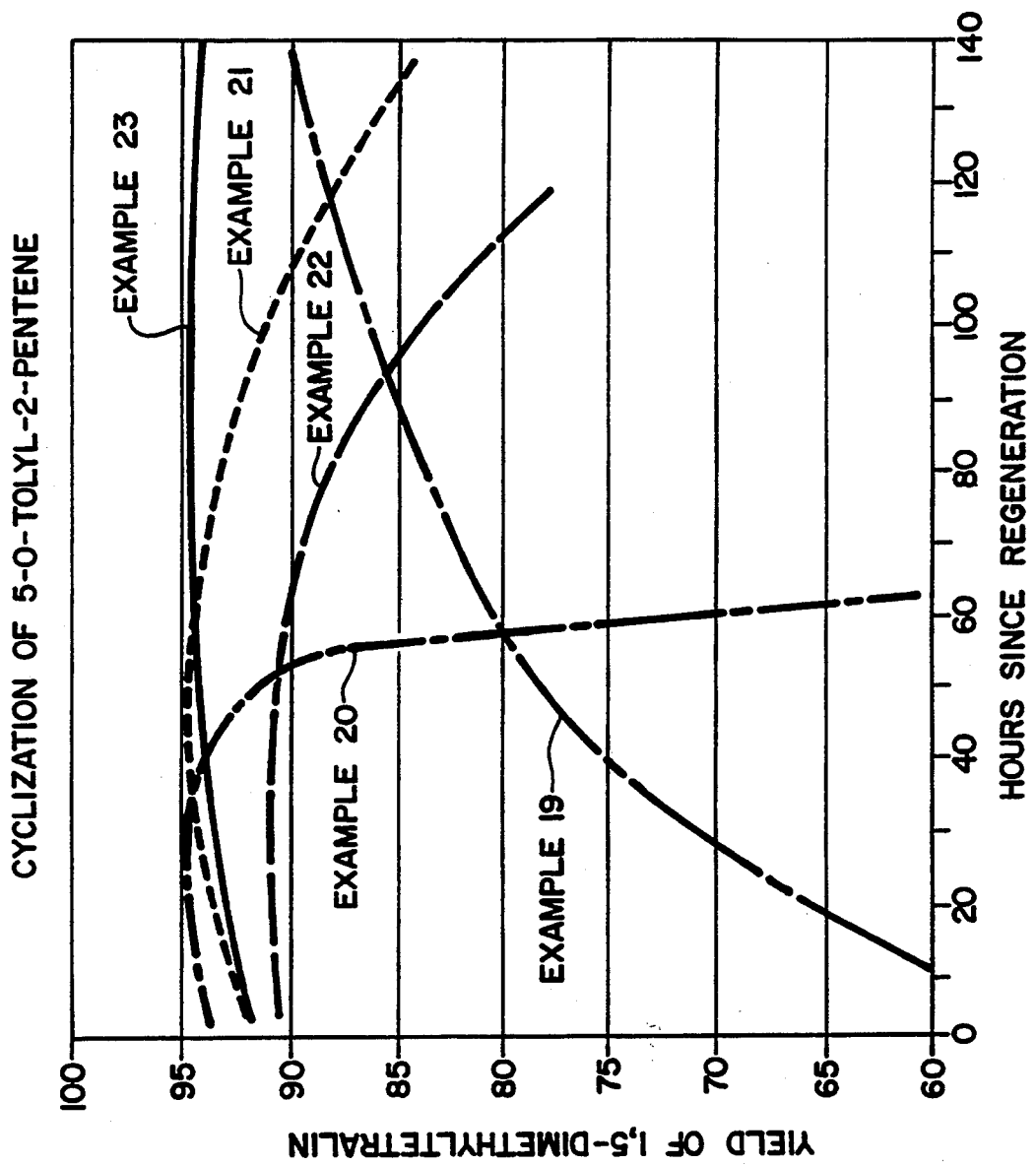

PREPARATION OF A DIMETHYLTETRALIN BY CYCLIZING AN ORTHOTOLYLPENTENE PHENYLHEXENE USING AN ULTRA-STABLE CRYSTALLINE ALUMINOSILICATE MOLECULAR SIEVE Y-ZEOLITE

This application is a continuation of U.S. patent application Ser. No. 07/794,018, filed on Nov. 19, 1991, now abandoned; which, in turn, is a continuation of U.S. patent application Ser. No. 07/633,068, filed on Dec. 21, 1990, now abandoned; which, in turn, is a continuation-in-part of related U.S. patent applications Ser. No. 07/539,007, filed on Jun. 15, 1990, now U.S. Pat. No. 5,030,781, and Ser. No. 07/539,087, filed on Jun. 15, 1990, now U.S. Pat. No. 5,034,561, and of U.S. patent application Ser. No. 07/556,297, filed on Jul. 20, 1990, now U.S. Pat. No. 5,073,670; wherein application Ser. No. 07/556,297, is a continuation-in-part of U.S. patent application Ser. No. 07/316,308, filed on Feb. 27, 1989, now U.S. Pat. No. 4,950,825; which, in turn, is a continuation-in-part of U.S. patent application Ser. No. 07/211,000, filed on Jun. 24, 1988, now abandoned.

FIELD OF THE INVENTION

This invention relates generally to a method for preparing a dimethyltetralin and more particularly concerns a method for preparing primarily a specific dimethyltetralin or a mixture of specific dimethyltetralins from either 5-(o-, m-, or p-tolyl)-pent-1- or -2-ene or 5-phenyl-hex-1- or -2-ene in the presence of a Y-type crystalline aluminosilicate molecular sieve zeolite.

DESCRIPTION OF PRIOR ART

Naphthalene dicarboxylic acids are monomers that are known to be useful for the preparation of a variety of polymers. For example, poly(ethylene 2,6-naphthalate) prepared from 2,6-naphthalene dicarboxylic acid and ethylene glycol has better heat resistance and mechanical properties than polyethylene terephthalate and is useful in the manufacture of films and fibers.

Dimethylnaphthalenes are desirable feedstocks for oxidation to the corresponding naphthalene dicarboxylic acids. A known conventional process for producing a naphthalene dicarboxylic acid comprises the oxidation of a dimethylnaphthalene with oxygen in the liquid phase in an acetic acid solvent at an elevated temperature and pressure and in the presence of a catalyst comprising cobalt, manganese and bromine components.

Typically dimethylnaphthalenes are found in refinery or coal-derived streams as mixtures of all of the ten possible dimethylnaphthalene isomers. However, separation of these isomers is very difficult and expensive. Consequently, methods for producing specific dimethylnaphthalenes or mixtures of two or three specific dimethylnaphthalenes in high purity and quality are highly desirable. One type of such method is a multistep synthesis involving (1) the formation of an alkenylbenzene by the reaction of o-, m- or p-xylene or ethylbenzene with butadiene, (2) the cyclization of the resulting alkenylbenzene to form one or more dimethyltetralins belonging to one or two of three groups of three isomeric dimethyltetralins—that is, either group A containing the 1,5-, 1,6-, 2,5- and 2,6-dimethyltetralins, group B containing the 1,7-, 1,8-, 2,7- and 2,8-dimethyltetralins, or group C containing the 1,3-, 1,4-, 2,3-, 5,7-, 5,8- and 6,7-dimethyltetralins—(3) the dehydrogenation of the dimethyltetralin(s) to form the corresponding dimethylnaphthalene(s), and (4) the isomerization of the resulting dimethylnaphthalene(s) to the desired specific dimethylnaphthalene.

For example, Thompson. U.S. Pat. Nos. 3,775,496; 3,775,497; 3,775,498; 3,775,500 disclose processes for the cyclization of specific alkenylbenzenes to one or more specific dimethyltetralins at 200°–450° C. in the presence of any suitable solid acidic cyclization catalyst such as acidic crystalline zeolites as well as silica-alumina, silica-magnesia and silica-alumina-zirconia and phosphoric acid, followed by the dehydrogenation of the resulting dimethyltetralin(s) in the vapor state to the corresponding dimethylnaphthalene(s) in a hydrogen atmosphere at 300°–500° C. and in the presence of a solid dehydrogenation catalyst such as noble metals on carriers and chromia-alumina, and thereafter isomerization of each of the aforesaid dimethylnaphthalene(s) to the desired isomer within the triad of dimethylnaphthalenes to which the isomer being isomerized belongs, at 275°–500° C. in the presence of a solid acidic isomerization catalyst of the same type as described in respect of the cyclization disclosed therein. In the alternative, both the cyclization and isomerization reactions can be performed in the liquid phase, in which case the cyclization is performed at 200°–275° C. with a solid phosphoric acid catalyst, at 70°–140° C. with an acidic ion exchange resin, an acidic crystalline zeolite, hydrofluoric or sulfuric acid as the catalyst or a siliceous cracking catalyst.

More specifically, Thompson, U.S. Pat. No. 3,775,496 discloses the cyclization of 5-(m-tolyl)-pent2-ene to 1,6- and 1,8-dimethyltetralins, which are then dehydrogenated to 1,6- and 1,8-dimethylnaphthalenes, which in turn are isomerized to 2,6- and 2,7-dimethylnaphthalenes, respectively. Thompson, U.S. Pat. No. 3,775,497 discloses the cyclization of 5-phenyl-hex-2-ene to 1,4-dimethyltetralin which is then dehydrogenated to 1,4-dimethylnaphthalene, which is in turn isomerized to 2,3-dimethylnaphthalene. Thompson, U.S. Pat. No. 3,775,498 discloses the cyclization of 5-(o-tolyl)-pent-2-ene to 1,5-dimethyltetralin, which is then dehydrogenated to 1,5-dimethylnaphthalene, which is in turn isomerized to 2,6-dimethylnaphthalene. Thompson, U.S. Pat. No. 3,775,500 discloses the cyclization of 5-(p-tolyl)-pent-2-ene to 1,7-dimethyltetralin, which is then dehydrogenated to 1,7-dimethylnaphthalene, which in turn is isomerized to 2,7-dimethylnaphthalene.

Shimada et al., U.S. Pat. No. 3,780,119 disclose a method for the isomerization of dimethylnaphthalene by the use at a temperature above 260° C. of a mordenite catalyst in which a metal form of mordenite is in excess of 20 weight percent of the mordenite, with the metal being selected from the group consisting of lithium, sodium, potassium, magnesium, calcium, strontium, barium, zinc and aluminum.

Suld et al., U.S. Pat. No. 3,803,253 disclose a method for the hydroisomerization of a dimethylnaphthalene by the use of a combination of a hydrogenation catalyst and a calcium-containing zeolite catalyst, such as a calcium-exchanged synthetic faujasite, for example, a Y-type molecular sieve.

Shima et al., U.S. Pat. No. 3,806,552 disclose a method for the isomerization of dimethylnaphthalenes in the gas phase by the use of a mixed catalyst consisting of (a) 65–95 weight percent of a hydrogen form of mordenite in which above 80 weight percent of the metal cations are replaced with hydrogen ions, and (b) 5–35 weight percent of catalyst selected from the group consisting of bentonite and fuller's earth.

Hedge, U.S. Pat. No. 3,855,328 discloses a method for the isomerization of dimethylnaphthalenes by the use of a Type Y alumino silicate zeolite at 120°–300° C. in the liquid phase. The catalysts have aluminum-to-silicon atomic ratios of 0.1–1.0.

Ogasawara et al., U.S. Pat. No. 3,888,938 disclose a method for the isomerization of dimethylnaphthalenes in the liquid phase by the use of a mixed catalyst consisting of (a) 70–95 weight percent of a hydrogen form of mordenite in which above 80 weight percent of the metal cations are replaced with hydrogen ions, and (b) 5–30 weight percent of a promoter selected from the group consisting of bentonite and fuller's earth.

Hedge et al., U.S. Pat. No. 3,928,482 disclose the isomerization of either dimethyldecalins, dimethyltetralins or dimethylnaphthalenes in the presence of an alumino silicate zeolite containing polyvalent metal cations in exchange positions, such as a rare earth-exchanged Type Y zeolite.

Yokayama et al., U.S. Pat. No. 3,957,896 disclose the selective isomerization of dimethylnaphthalenes in the presence of any kind of natural or synthetic, solid acid catalyst, such as Y-type zeolite as well as silica-alumina, silica-magnesia, silica-zirconia, silica-alumina-zirconia, fuller's earth, natural or synthetic mordenite, X-type zeolite, A-type zeolite and L-type zeolite. These catalysts may be substituted partly or wholly by hydrogen or metal. Furthermore, these catalysts can be unsupported or supported on carriers.

Onodera et al., U.S. Pat. No. 4,524,055 disclose a crystalline aluminosilicate zeolite that is useful in the isomerization of dimethylnaphthalenes and has a silica-to-alumina mole ratio of 10 to 100, specific x-ray lattice distances, and a specific cyclohexane-to-n-hexane adsorption ratio of at least 0.7.

Maki et al., U.S. Pat. No. 4,556,751 disclose the isomerization of dimethylnaphthalenes in the presence of a crystalline aluminosilicate having a pentasil structure and a silica-to-alumina molar structure of 12 or higher. In addition, the aluminosilicate may contain some other metals as non-exchangeable metals.

A problem in all such prior art methods is the presence of other dimethylnaphthalene isomers and unconverted dimethyltetralin and alkenylbenzene as impurities and by-products in the finally obtained, desired specific dimethylnaphthalene isomer. The presence of such impurities and by-products markedly reduces the utility and commercial value of the desired dimethylnaphthalene isomer, especially as a precursor for the formation of a naphthalene dicarboxylic acid for use as a monomer in the manufacture of a polymer. In addition, catalysts tend to deactivate relatively rapidly at the high temperatures employed in vapor phase processes. Therefore, it is highly desirable to employ liquid phase processes and to improve the completeness of each step in the aforesaid multistep synthesis and the selectivity of each step therein for the production of the desired product therefrom.

In this regard, it is known that in the presence of an acid catalyst, the dimethylnaphthalene isomers are isomerizable within each triad of dimethylnaphthalene isomers—that is, within the 1,5-, 1,6- and 2,6-dimethylnaphthalenes of triad A, within the 1,7-, 1,8-, and 2,7-dimethylnaphthalenes of triad B, and within the 1,3-, 1,4- and 2,3-dimethylnaphthalenes of triad C. It is also known that the interconversion of a dimethylnaphthalene isomer within one of the aforesaid triads to a dimethylnaphthalene isomer within another of the aforesaid triads occurs to a relatively lesser extent. Consequently, it is highly desired to improve the selectivity of the cyclization step in the aforesaid multistep synthesis for the formation of dimethyltetralin isomers that belong to the same triad to which also belongs the specific desired dimethyltetralin isomer, which upon dehydrogenation is converted to the desired specific corresponding dimethylnaphthalene isomer. It is also highly desired to improve the selectivity and completeness of the isomerization step in the aforesaid multistep synthesis for the formation of the specific dimethylnaphthalene isomer desired.

OBJECTS OF THE INVENTION

It is therefore a general object of the present invention to provide an improved method for manufacturing with an improved yield and selectivity a specific dimethyltetralin isomer or set of dimethyltetralin isomers by the cyclization of an alkenylbenzene which meets the aforementioned requirements for selectivity and completeness and catalyst activity.

It is a related object of the present invention to provide an improved method for manufacturing with an improved yield and selectivity a specific dimethylnaphthalene isomer or set of dimethylnaphthalene isomers by the cyclization of an alkenylbenzene to form a specific dimethyltetralin isomer or set of dimethyltetralin isomers and then dehydrogenating the dimethyltetralin(s).

It is another related object of the present invention to provide an improved method for manufacturing with an improved yield and selectivity a specific dimethylnaphthalene isomer or set of specific dimethylnaphthalene isomers by the cyclization of an alkenylbenzene to form a specific dimethyltetralin isomer or set of dimethyltetralin isomers and then dehydrogenating the dimethyltetralin(s) and isomerizing the resulting dimethylnaphthalene(s).

Other objects and advantages of the method of the present invention will become apparent upon reading the following detailed description and appended claims.

SUMMARY OF THE INVENTION

The objects are achieved by an improved method for preparing a dimethyltetralin (DMT) from 5-(o-, m-, or p-tolyl)-pent-1- or -2-ene or 5-phenyl-hex-1- or -2-ene as the first feedstock, comprising: contacting the first feedstock in liquid form with a solid cyclization catalyst comprising a Y-type, crystalline aluminosilicate molecular sieve zeolite that is substantially free of adsorbed water, and at an elevated temperature and at a pressure that is sufficiently high to maintain the first feedstock substantially in the liquid phase, to thereby cyclize the first feedstock to form a first liquid product comprising a mixture of dimethyltetralins, wherein, if present, the concentration of water in the first feedstock is less than about 0.5 weight percent, based on the weight of the feedstock, wherein either (a) the first feedstock comprises 5-(o-tolyl)-pent-1- or -2-ene and 1,5-, 1,6-, 2,5- or 2,6-dimethyltetralin or mixtures thereof comprise at least 80 weight percent of the mixture of dimethyltetralins formed, (b) the first feedstock comprises 5-(m-tolyl)-pent-1- or -2-ene and 1,5-, 1,6-, 1,7-, 1,8-, 2,5-, 2,6-, 2,7-, or 2,8-dimethyltetralin, or mixtures thereof comprise at least 80 weight percent of the mixture of dimethyltetralins formed, (c) the first feedstock comprises 5-(p-tolyl)-pent-1- or -2-ene and 1,7-, 1,8-, 2,7-, or 2,8-dimethyltetralin, or mixtures thereof comprise at least 80 weight percent of the mixture of dimethyltetralins formed, (d) the first feedstock comprises 5-phenyl-1- or -2-hexene and 1,3-, 1,4-, 2,3-, 5,7-, 5,8- or 6,7-dimethyltetralin or mixtures thereof comprise at least 80 weight percent of the mixture of dimethyltetralins formed.

This invention is also a method for preparing one or more dimethyltetralins from 5-(o-, m-, or p-tolyl)-pent-1- or -2-ene or 5-phenyl-hex-1- or -2-ene as the first feedstock, comprising: contacting the first feedstock in liquid form with a solid cyclization catalyst comprising an ultra-stable crystalline aluminosilicate molecular sieve Y-zeolite that has a silica-to-alumina molar ratio of from about 3:1 to about 200:1, pore windows provided by twelve-membered rings containing oxygen and a unit cell size of from about 24.0 to about 24.7 Angstroms, and that contains from about 0.01 up to about 3.5 weight percent of sodium, calculated as elemental sodium, and based on the weight of the zeolite and that is substantially free of adsorbed water, and at an elevated temperature and at a pressure that is sufficiently high to maintain the first feedstock substantially in the liquid phase, to thereby cyclize the first feedstock to form a first liquid product comprising one or more dimethyltetralins, wherein water is at a concentration in the first feedstock of from zero up to less than about 0.5 weight percent, based on the weight of the feedstock, wherein (1) when the first feedstock comprises 5-(o-tolyl)-pent-1- or -2-ene, at least 80 weight percent of the dimethyltetralin product formed is comprised by 1,5-, 1,6-, 2,5- or 2,6-dimethyltetralin or a mixture thereof, (2) when the first feed stock comprises 5-(m-tolyl)-pent-1- or -2-ene, at least 80 weight percent of the dimethyltetralin product formed is comprised by 1,5-, 1,6-, 1,7-, 1,8-, 2,5-, 2,6-, 2,7- or 2,8-dimethyltetralin or a mixture thereof, (3) when the first feedstock comprises 5-(p-tolyl)-pent-1- or -2-ene, at least 80 weight percent of the dimethyltetralin product formed is comprised by 1,7-, 1,8-, 2,7- or 2,8-dimethyltetralin or a mixture thereof, or (4) when the first feedstock comprises 5-phenyl-hex-1- or -2-ene, at least 80 weight percent of the dimethyltetralin product formed is comprised of 1,3-, 1,4-, 2,3-, 5,7-, 5,8- or 6,7-dimethyltetralin or a mixture thereof.

In another aspect, this invention is an improved method for preparing one or more dimethyltetralins from 5-(o-, m-, or p-tolyl)-pent-1- or -2-ene or 5-phenyl-hex-1- or -2-ene as the first feedstock, comprising: (a) contacting the first feedstock in liquid form with a solid cyclization catalyst comprising a crystalline aluminosilicate molecular sieve Y-zeolite that is substantially free of adsorbed water, and having a silica-to-alumina bulk molar ratio in the range of about 3:1 to about 200:1, pore windows provided by twelve-membered rings containing oxygen, a unit cell size in the range of about 24.0 to about 24.7 Angstroms, and a sodium content of about 0.01 to about 3.5 weight percent, calculated as elemental sodium and based on the weight of the zeolite; at an elevated temperature and at a pressure that is sufficiently high to maintain the feedstock substantially in the liquid phase to thereby cyclize the first feedstock to form a liquid product comprising one or more dimethyltetralins, wherein water is at a concentration in the feedstock of from 0.0 up to less than about 0.5 weight percent, based on the weight of the feedstock, wherein (1) when the first feedstock comprises 5-(o-tolyl)-pent-1- or -2-ene, at least 80 weight percent of the dimethyltetralin product formed is comprised of 1,5-, 1,6-, 2,5- or 2,6-dimethyltetralin, (2) when the first feedstock comprises 5-(m-tolyl)-pent-1- or -2-ene, at least 80 weight percent of the dimethyltetralin product formed is comprised of 1,5-, 1,6-, 1,7-, 1,8-, 2,5-, 2,6-, 2,7- or 2,8-dimethyltetralin or a mixture thereof, (3) when the first feedstock comprises 5-(p-tolyl)-pent-1- or -2-ene, at least 80 weight percent of the dimethyltetralin product formed is comprised of 1,7-, 1,8-, 2,7- or 2,8-dimethyltetralin or a mixture thereof, and (4) when first feedstock comprises 5-phenyl-1- or -2-hexene, at least 80 weight percent of the dimethyltetralin product formed is comprised of 1,3-, 1,4-, 2,3-, 5,7-, 5,8- or 6,7-dimethyltetralin or a mixture thereof; (b) separating the resulting cyclization product mixture by distillation at reduced pressure such that a lighter fraction comprising the dimethyltetralin product is separated as the overhead from a heaver fraction comprising materials boiling above the dimethyltetralins; and (c) combining the resulting heavier fraction with a fresh supply of the tolylpentene(s) or phenyl-hexene(s) employed in step (a) and cyclizing the resulting mixture under the cyclization conditions recited in step (a).

BRIEF DESCRIPTION OF THE DRAWING

For a more complete understanding of this invention, reference should now be made to the embodiments illustrated in greater detail by the results presented in the accompanying drawing and described below by way of examples of the invention. In the drawing, FIG. 1 is a series of plots of the yields of 1,5-dimethyltetralin from the cyclization of 5-o-tolyl-2-pentene in Examples 19–23 involving 5 different cyclization catalysts.

DETAILED DESCRIPTION OF THE PREFERRED EMBODIMENTS

Suitable feedstocks for use in the cyclization of the method of the present invention are 5-(o-, m-, or p-tolyl)-pent-1- or -2-ene or 5-phenyl-hex-1- or -2-ene. In the method of the present invention, the cyclization step is followed preferably by a dehydrogenation step and more preferably by first a dehydrogenation step and second an isomerization step.

When 5-(o-tolyl)-pent-1- or -2-ene is the feedstock to the cyclization step of the present invention, 1,5-, 1,6-, 2,5-, or 2,6-dimethyltetralin or a mixture thereof comprises at least 80, preferably at least 85 weight percent of the dimethyltetralins produced therefrom, which resulting dimethyltetralins are in turn the feedstock and are converted in the dehydrogenation step of the present invention to the corresponding 1,5-, 1,6- and 2,6-dimethylnaphthalenes (DMNs), which are then the feedstock in the isomerization step of the present invention and are converted therein to 2,6-dimethylnaphthalene.

When 5-(m-tolyl)-pent-1- or -2-ene is the feedstock to the cyclization step, 1,5- 1,6- 1,7-, 1,8- 2,5- 2,6-, 2,7- or 2,8-dimethyltetralin or a mixture thereof comprises at least 80, preferably at least 85 weight percent of the dimethyltetralins produced therefrom, which dimethyltetralins are in turn the feedstock and are converted in the dehydrogenation step to the corresponding 1,5-, 1,6-, 1,7-, 1,8- 2,6- and 2,7-dimethylnaphthalenes, which are then the feedstock in the isomerization step and are converted to 2,6- and 2,7-dimethylnaphthalenes.

When 5-(p-tolyl)-pent-1- or -2-ene is the feedstock to the cyclization step, 1,7-, 1,8-, 2,7- or 2,8-dimethyltetralin or a mixture thereof comprises at least 80, preferably at least 85 weight percent of the dimethyltetralins produced therefrom, which dimethyltetralins are in turn the feedstock and are converted in the dehydrogenation step to the corresponding 1,7-, 1,8- and 2,7-dimethylnaphthalenes which are then the feedstock and are converted in the isomerization step to 2,7-dimethylnaphthalene.

When 5-phenyl-1- or -2-hexene is the feedstock to the cyclization step, 1,3-, 1,4-, 2,3-, 5,7, 5,8-, or 6,7-dimethyltetralin or a mixture thereof comprises at least 80, preferably at least 85 weight percent of the dimethyltetralins produced therefrom, which dimethyltetralins are in turn the feedstock and are converted in the dehydrogenation step to the corresponding, 1,3-, 1,4- and 2,3-dimethylnaphthalenes, which are then the feedstock in the isomerization step and are convened to 2,3-dimethylnaphthalene.

In the method of the present invention, each of the aforesaid cyclization, dehydrogenation and isomerization reactions is performed in the liquid phase at an elevated temperature and at a sufficiently high pressure to ensure that the feedstock for the particular step is maintained in the liquid phase. By elevated temperature it is meant a temperature sufficiently high so that a significant portion of the feedstock for the respective reaction is converted to the desired product using preselected catalyst levels and reaction times for batch processes, or preselected space velocities for continuous processes. Preferably, the cyclization reaction is performed at a temperature in the range of about 120° C., more preferably about 150° C., to about 400° C., more preferably to about 350° C. Most preferably the cyclization reaction is performed at a temperature in the range of about 150° C. to about 300° C. The cyclization reaction is preferably performed at a pressure in the range of about 0.05, more preferably about 0.1, to about 20.0, more preferably to about 5.0 atmospheres absolute. The dehydrogenation reaction is preferably performed at a temperature in the range of about 200° C., more preferably about 220° C., to about 500° C., more preferably to about 450° C. Most preferably, the dehydrogenation reaction is performed at a temperature in the range of about 220° C. to about 420° C. Preferably, the dehydrogenation reaction is performed at a pressure in the range of about 0.1, more preferably about 1.0, to about 30.0, more preferably to about 20.0 atmospheres absolute. The isomerization reaction is preferably performed at a temperature in the range of about 200° C., more preferably about 240° C., to about 420° C., more preferably to about 380° C. Most preferably the isomerization reaction is performed at a temperature in the range of about 240° C. to about 350° C. The isomerization reaction is preferably performed at a pressure in the range of about 0.1, more preferably about 0.5, to about 20.0, more preferably 5.0 atmospheres absolute.

Each of the cyclization, dehydrogenation and isomerization reactions can be performed with or without a solvent for the respective feedstock. Preferably a solvent is not employed in the aforesaid steps. If employed, a solvent in any of the aforesaid steps must be inert under the conditions employed and suitably comprise a paraffin such as a tetradecane, or an aromatic hydrocarbon such as anthracene, or mixtures thereof, which preferably boils above about 270° C. In the cyclization step, if water is present, its concentration is less than 0.5 weight percent, preferably less than 0.1 weight percent, based on the weight of the alkenylbenzene feedstock. More preferably, water is not present in the cyclization reaction medium.

Each of the cyclization, dehydrogenation and isomerization steps of the method of the present invention can be performed either batchwise or continuously. The reaction apparatus to be used in each aforesaid step can be of any known type such as a fixed bed, moving bed, fluidized bed, liquid phase suspended bed or a solid-liquid mixture in a stirred tank. Generally, however, the use of a fixed bed is commercially preferred for continuous operation. When conducting the dehydrogenation reaction of this invention in a continuous manner, it is advantageous to use two or more fixed bed reactors in series. Hydrogen formed during the dehydrogenation reaction is preferably removed from the product mixture between such fixed bed reactors arranged in series.

The improved conversion of the feedstock and selectivity for the production of the desired product or set of products for each of the cyclization, dehydrogenation and isomerization steps of the method of this invention are the result of the temperature and pressure conditions employed and the high activity and selectivity of the catalysts employed in each aforesaid step, which in turn permits the use of less severs conditions such that greater selectivity and reduced catalyst deactivation can be achieved.

The catalyst employed in the cyclization method of this invention comprises an ultrastable—that is, a thermally stabilized or dealuminated—crystalline aluminosilicate Y-zeolite having a silica-to-alumina bulk molar ratio in the range of from about 3:1, preferably from about 12:1, to about 200:1, preferably to about 100:1. having pore windows provided by twelve-membered rings containing oxygen and a unit cell size in the range of from about 24.0, preferably from about 24.1, to about 24.7, preferably to about 24.6 Angstroms, having a sodium content of from about 0.01 to about 3.5 weight percent, calculated as elemental sodium and based on the weight of the zeolite.

The term "relatively low acidity" as used herein in reference to a zeolite useful for the practice of this invention has reference to the relatively few Bronsted acid sites in the crystalline zeolite framework that provide sufficient acidity to catalyze the desired cyclization but without the production of undesirably large amounts of by-products. Substances that owe their acidity to the presence of protons are termed Bronsted acids. In the case of crystalline aluminosilicates or zeolites, a Bronsted acid site occurs in the crystalline zeolite framework where an aluminum atom surrounded by four oxygen atoms is present. Inasmuch as some of such Bronsted acid sites are neutralized by alkali metal present in the crystalline framework, the Bronsted acidity of a particular zeolite can be delineated by specifying the bulk molar ratios of silica-to-alumina and sodium oxide-to-alumina as set forth herein. In terms of the number of framework Bronsted acid sites per unit cell of the crystalline zeolite catalyst, for the purposes of the present method the catalyst has an average of no more than 10 framework Bronsted acid sites, preferably no more than about 4 such sites, per unit cell.

The term "ultrastable" as used herein in reference to a zeolite has reference to a zeolite which has been thermally stabilized or dealuminated to produce a synthetic zeolite having much improved resistance to degradation under acid and hydrothermal conditions. The term "zeolite Y" as used herein in reference to the contemplated crystalline aluminosilicate molecular sieve has reference to a zeolite which has the characteristic framework structure of the faujasite mineral class. The term "bulk molar ratio" as used herein denotes the molar ratio of the designated moieties regardless of whether present in the crystalline framework of the molecular sieve or not.

One preferred catalyst employed in the cyclization and/or cracking step of the method of this invention comprises an acidic ultrastable—that is, a thermally stabilized or dealuminated—Y-type crystalline aluminosilicate zeolite having a silica-to-alumina molar ratio of from about 4:1, preferably from about 5:1, to about 10:1, preferably to about 6:1, and having pore windows provided by twelve-membered rings containing oxygen, and a unit cell size of from about 24.2, preferably from about 24.3, to about 24.7, preferably to about 24.6 Angstroms. A suitable such zeolite is marketed by Union Carbide under the name LZ-Y72 or LZ-Y20.

The aforesaid acidic zeolite employed in the catalyst for the cyclization step of the method of this invention is in the hydrogen form and contains from about 0.05, up to about 3.5 weight percent of sodium, calculated as elemental sodium and based on the weight of the zeolite. If the cyclization step is performed batchwise, the cyclization catalyst preferably contains from about 1 to about 3.5 weight percent of sodium, calculated as elemental sodium and based on the weight of the zeolite. If the cyclization step is performed continuously, the cyclization catalyst preferably contains from about 0.05 to about 0.5 weight percent, calculated as elemental sodium and based on the weight of the zeolite. Preferably, the cyclization catalyst contains from about 0.01, preferably from about 0.05, to about 3, preferably to about 1.5 weight percent of a component comprising a first metal selected from the group consisting of platinum, palladium, iridium and rhodium, calculated as the elemental metal and based on the weight of the catalyst. Most preferably this metal component comprises platinum.

More preferably, especially when the cyclization is performed continuously, this cyclization catalyst also contains from about 0.01, preferably from about 1, to about 5, preferably to about 3 weight percent of a component comprising a second metal selected from the group consisting of copper, tin, gold, lead and silver, calculated as the elemental metal and based on the weight of the catalyst. More preferably this second metal component comprises copper, tin or gold.

A most preferred type of catalyst for use as the cyclization catalyst and/or the cracking catalyst in the method of this invention is another ultrastable zeolite Y in the hydrogen form and having a relatively low acidity that has relatively lower alumina and sodium oxide contents. The catalyst framework alumina concentration for such zeolite is indicated in part by the unit cell size which, as measured by x-ray diffraction, is no more than 24.3 Angstroms. The silica-to-alumina bulk molar ratio is at least about 12:1, at least about 20:1 and most preferably at least about 30:1. The sodium oxide-to-alumina bulk molar ratio is in the range of from about 0.001:1, preferably from about 0.01:1, to about 1:1, preferably to about 0.05:1. The sodium content of this zeolite is less than about 0.4, preferably less than about 0.23 weight percent, based on the weight of the zeolite and calculated as elemental sodium. Commercially available examples of this type of preferred zeolite are Conteka CBV 760 obtained from Conteka Company, Leiden, the Netherlands, and Valfor CP 301-26 obtained from PQ Corporation, Valley Forge, Pa. Conteka CBV 760 has a sodium oxide-to-alumina bulk molar ratio of about 0.05:1, a silica-to-alumina bulk molar ratio of about 50:1, and a sodium content of about 0.08 weight percent based on the weight of the zeolite and calculated as elemental sodium, has a unit cell size of 24.2 Angstroms and a specific surface area of 720 square meters per gram, and is in powder form. Valfor CP 301-26 has a sodium-oxide-to-alumina bulk molar ratio of about 0.02:1, a silica-to-alumina bulk molar ratio of about 80:1, a sodium content of about 0.02 weight percent based on the weight of the zeolite and calculated as elemental sodium, a unit cell size of 24.25 Angstroms, and a specific surface area of about 775 square meters per gram, and is also in powder form.

When using this relatively low acidity, lower alumina and lower sodium oxide zeolite Y catalyst it is preferable that the alkenylbenzene feedstream contain no more than about 0.1 weight percent water.

The zeolites are preferably substantially free of adsorbed water. If present on the zeolite, the adsorbed water can be removed from the zeolite by heating it in a dry atmosphere at about 250° C. for 0.5–1 hour. In the alternative, and less preferably, the presence of absorbed water at a concentration of up to 15 weight percent of the catalyst can be tolerated if a reaction temperature in the aforesaid range of at least 180° C. is employed.

The aforesaid zeolites can be employed either unsupported or supported on a porous refractory, inorganic oxide that is inert under the conditions employed, such as silica, alumina, silica-alumina, magnesia, bentonite or other such clays. If a support is employed, preferably the support comprises silica, alumina, or silica-alumina. When a support is employed, the zeolite comprises from about 10, preferably from about 20, to about 90, preferably to about 80 weight percent based on the weight of the catalyst.

If the cyclization is performed on a batch basis, the catalyst is employed at a level in the range of from about 0.1, preferably from about 1.0, to about 5, preferably to about 3 weight percent of the zeolite component of the catalyst, based on the weight of the alkenylbenzene feedstock, and the reaction time is from about 0.5, preferably from about 2, to about 10, preferably to about 6 hours. If the cyclization is performed on a continuous basis, the space velocity is in the range of from about 0.1, preferably from about 1, to about 100, preferably to about 50, parts of alkenylbenzene feedstock per part of zeolite component of the catalyst by weight per hour.

The zeolite catalyst used in the method of the present invention can be either in a powdered form or in a granular form. A powdered catalyst is conveniently mechanically dispersed by mixing action in the liquid phase reactant employed. When in a granular form, the granule size can vary widely, such as from about 0.03-inch to about 1 inch in average maximum diameter, the exact size in any given instance being influenced by the choice of particular fixed-bed reactor wherein the granular form is to be employed and through which the liquid phase reactant is circulated. As used herein, the term "granular form" is generic to porous structures having the various possible physical shapes, and made by the various possible physical shapes, and made by the various possible preparation methods, including compacting, extruding, and the like, and such term is inclusive of both supported and unsupported zeolite catalyst forms.

In one embodiment of this invention, under conditions at which the cyclization reaction is substantially complete, the resulting cyclization product mixture can be separated by distillation at reduced pressure into a relatively lighter (or lower boiling) fraction that contains the dimethyltetralin product and a relatively heavier (or higher boiling) fraction that boils above the boiling point(s) of the dimethyltetralin product. The reduced pressure is preferably in the range of from about 0.03 up to less than about 1.0 atmosphere. The heavier fraction boils preferably above 240° C. and more preferably above 250° C. at atmospheric pressure.

The heavier fraction of the aforesaid cyclization product mixture, which is the distillation bottom, remains in the cyclization reactor or is recycled to it, and is next combined with a fresh supply of the tolyl-pentene(s) or phenyl-hexene(s) employed as the feedstock in the aforesaid cyclization step, and the resulting mixture is subjected to the aforesaid cyclization conditions. Under conditions at which the cyclization reaction is substantially complete, the resulting cyclization product mixture is separated by distillation at reduced pressure into a relatively lighter (or lower boiling) fraction that contains the dimethyltetralin product and a relatively heavier (or higher boiling) fraction that boils above the boiling points of the dimethyltetralin product. The reduced pressure is preferably in the range of from about 0.03 up to about 1.0 atmosphere. The heavier fraction boils preferably above 240° C. and more preferably above 250° C. at atmospheric pressure. In a preferred embodiment of the method of this invention, either immediately after the cyclization or at least ultimately, the lighter fraction, which is the distillate, is dehydrogenated such that the dimethyltetralin(s) therein are convened to the corresponding dimethylnaphthalenes. Again, the heavier fraction of the cyclization product mixture, which generally is the distillation bottoms, remains in the cyclization reactor or is recycled to it, and is combined with a fresh supply of the tolyl-pentene(s) or phenyl-hexene(s) employed as the feedstock in the aforesaid cyclization step, and the resulting mixture is subjected to the aforesaid cyclization conditions. In a batch operation, the heavier fraction and fresh supply of tolyl-pentene(s) or phenyl-hexene(s) are combined at a ratio of from about 0.01 part, preferably from about 0.05 part, to about 2, preferably to about 0.35 parts, by weight of the heavier fraction per part of the aforesaid fresh supply. In a continuous operation, the heavier fraction and the fresh supply of tolyl-pentene(s) or phenyl-hexane(s) are combined at a ratio of from about 0.2 part, preferably from about 1 part to about 20 parts, preferably to about 5 parts by weight of the heavier fraction per part of fresh supply.

This sequence of cyclization of a mixture of fresh tolyl-pentene(s) or phenyl-hexene(s) and the distillation bottoms of the reduced pressure distillation of the products from the previous cyclization run, followed by reduced pressure distillation of the resulting cyclization products and combination of the resulting distillation bottoms with fresh tolyl-pentene(s) or phenyl-hexene(s) can be repeated until the activity of the cyclization catalyst declines to such an extent that the reaction times become excessive. Typically, in a batch operation this sequence of cyclization, separation and recycle of the distillation bottoms to the cyclization step is repeated up to 100 times, preferably from 5 to 30 times for a given charge of catalyst. Typically, in a continuous operation, relatively small amounts of the catalyst would be removed from the reactor and replaced in the reactor with fresh catalyst in order to maintain the desired catalyst activity.

At the end of a continuous cyclization run or at the end of a series of batch cyclization runs, the distillation bottoms from the last reduced pressure distillation can be subjected to cracking at a temperature in the range of from about 120° C., preferably from about 180° C., to about 450° C., preferably to about 330° C., which temperature is higher than the temperature at which the cyclization was performed by at least 10° C., preferably by at least 30° C. The cracking operation is performed at a pressure that is sufficiently high so that the materials being cracked are substantially in the liquid phase, and generally the pressure is from about 0.03, preferably from about 0.1, to about 10, preferably to about 2.0, atmospheres absolute. The cracking operation can be performed using as the cracking catalyst the same catalyst that had been employed as the cyclization catalyst. In the alternative, suitable cracking catalysts include any catalyst that is conventionally employed for acid-catalyzed reactions, such as silica-alumina, acidic molecular sieves, mineral acids or acidic ion exchange resins.

The resulting cracked products include dimethyltetralins which are then separated by distillation at a reduced pressure in the range of from about 0.03 to less than about 1.0 atmosphere into a lighter (or lower boiling) fraction which contains the dimethyltetralin product and a relatively heavier (or higher boiling) fraction that boils above the boiling point(s) of the dimethyltetralin product. In a preferred embodiment of the method of this invention either immediately after the cracking treatment or at least ultimately, the lighter fraction which is the distillate is dehydrogenated to convert the dimethyltetralins therein to dimethylnaphthalenes. Thus, cracking the distillate bottoms from the last cyclization enhances the degree of the conversion of the tolyl-pentene(s) or phenyl-hexene(s) to dimethyltetralins, and, after the combination of cyclization, distillation and dehydrogenation steps, of dimethylnaphthalenes. Similarly, the heavy cracked products which remain as the distillate bottoms after the combination of cyclization and distillation steps represent only a minor fraction of the total amount of comparably heavy materials that would have been produced in an equal number of cyclization and without subjecting the heavy cyclization products to further treatment in accordance with this method of this invention. Thus, this embodiment produces greater relative amounts of useful dimethylnaphthalenes and produces a cyclization product mixture distillate as feedstock for subsequent dehydrogenation, which distillate contains substantially smaller amounts of relatively heavier cyclization products which have an adverse effect on the subsequent dehydrogenation and isomerization steps.

The catalyst employed in the dehydrogenation step of the method of this invention is any solid dehydrogenation catalyst that is capable of effecting the dehydrogenation and exhibiting a reasonable lifetime under the conditions employed, including catalysts such as noble metals on carriers such as reforming catalysts. Aluminas, silicas, alumina-silicas, and activated carbons are examples of suitable carriers or supports. The noble metals include, for example, platinum, palladium, ruthenium and rhenium. The noble metal component can also comprise mixtures of two or more noble metals. Preferably, palladium on an active carbon or alumina support containing from about 0.5, more preferably from about 1.0, to about 15, more preferably to about 10 weight percent of palladium, calculated as elemental palladium and based on the weight of the catalyst, is employed as the dehydrogenation catalyst.

Other preferred dehydrogenation catalysts include platinum on activated carbon or alumina supports, rhenium on activated carbon or alumina supports and mixtures of platinum and rhenium on activated carbon or alumina supports, wherein the platinum and rhenium are each present from about 0.01, preferably 0.05, to about 10.0, preferably 5.0 weight percent calculated as the element and based on the weight of the catalyst. A more preferred dehydrogenation catalyst comprises a mixture of platinum and rhenium on gamma alumina where the platinum and rhenium are each present in the range of about 0.1 to about 1.0 weight percent calculated as the element, and based on the weight of the catalyst. A support material such as an alumina or other non-combustible support material has an advantage over a carbon support material in that the non-combustible support can be exposed to air or other source of oxygen-containing gas at an elevated temperature to regenerate a deactivated catalyst. Consequently, such a catalyst can be cycled wherein between each cycle of use as a dehydrogenation catalyst the catalyst is regenerated with an oxygen-containing gas at an elevated temperature. Preferably the level of oxygen in the oxygen-containing gas is about 1 wt % to about 25 wt %, the regeneration temperature is in the range of about 400° C. to about 600° C. and the time of exposure to the oxygen-containing gas at these temperatures is that sufficient to regenerate the catalyst.

In the liquid phase dehydrogenation reactions of this invention, when conducted in either a batch or continuous manner, and particularly when using the preferred dehydrogenation catalysts, the addition of hydrogen to the reaction mixture is not necessary to maintain catalyst activity during extended catalyst use, i.e., the liquid phase dehydrogenation reaction in the method of this invention wherein a dimethyltetralin is dehydrogenated to a dimethylnaphthalene proceeds in the absence of hydrogen added to the reaction mixture. Without intending to be bound by a theory of operation, it appears that during the liquid phase dehydrogenation method of this invention wherein dimethyltetralins are dehydrogenated to dimethylnaphthalenes using a dehydrogenation catalyst, and particularly the preferred noble metal dehydrogenation catalysts disclosed herein, the hydrogen generated during the dehydrogenation reaction effectively maintains catalyst activity.

In the dehydrogenation method of this invention it is however advantageous to remove at least some hydrogen during the liquid phase dehydrogenation reaction. This is accomplished in a batch procedure by venting the hydrogen from the vessel used to conduct the batch reaction. If operating in a continuous mode, a plurality of series arranged fixed bed reactors can be utilized with the hydrogen vented from the process stream between fixed bed reactors.

If the dehydrogenation is performed on a batch basis, the catalyst is employed at a level in the range of from about 0.005, preferably from about 0.01, to about 1.0, preferably to about 0.2 weight percent of the noble metal component, calculated as the elemental noble metal and based on the weight of the dimethyltetralin feedstock, and the reaction time is from about 1, preferably from about 2, to about 50, preferably to about 40 hours. If the dehydrogenation is performed on a continuous basis, the space velocity is in the range of from about 0.1, preferably from about 10, to about 5000, preferably to about 2000 parts of the dimethyltetralin feedstock per part of the noble metal component (calculated as the elemental noble metal) of the catalyst by weight per hour.

The catalyst employed in the isomerization step of the method of this invention comprises either beta zeolite or an acidic ultrastable—that is, a thermally stabilized or dealuminated—Y-type crystalline aluminosilicate zeolite having a silica-to-alumina molar ratio of from about 4:1 preferably from about 5:1, to about 10:1, preferably to about 6:1, and having pore windows provided by twelve-membered rings containing oxygen, and a unit cell size of from about 24.2, preferably from about 24.3, to about 24.7, preferably to about 24.6 Angstroms. A suitable such zeolite is marketed by Union Carbide under the name LZ-Y72 or LZ-Y20. Water is not detrimental to catalytic activity or selectivity in the isomerization process.

The isomerization catalyst preferably comprises beta zeolite. The composition, structure and preparation of beta zeolite are described in Wadlinger et al., U.S. Pat. No. 3,308,069 which in its entirety is specifically incorporated herein by reference. The structure of beta zeolite is also reported in J. Haggin, "Structure of Zeolite Beta Determined," in Chemical & Engineering News, p. 23 (Jun. 20, 1988). Beta zeolite is also commercially available from PQ Corporation.

The aforesaid ultrastable Y-type zeolite which can be employed in the catalyst for the isomerization step of the method of this invention is in the hydrogen form and contains from about 0.01, preferably from about 1, up to about 5, preferably up to about 3, weight percent of sodium, calculated as elemental sodium and based on the weight of the zeolite.

Preferably the isomerization catalyst comprises a hydrogenation component comprising a Group VIII metal, which more preferably is palladium, platinum or nickel.

The aforesaid zeolite of the isomerization catalyst can be employed either unsupported or supported on a porous refractory, inorganic oxide that is inert under the conditions employed, such as silica, alumina, silica-alumina, magnesia, bentonite or other such clays. If a support is employed, preferably the support comprises silica, alumina or silica-alumina. When a support is employed, the zeolite comprises from about 10, preferably from about 20, to about 90, preferably to about 80 weight percent based on the weight of the catalyst.

If the isomerization is performed on a batch basis, the catalyst is employed at a level in the range of from about 0.1, preferably from about 1.0, to about 5, preferably to about 3 weight percent of the zeolite component of the catalyst, based on the weight of the dimethylnaphthalene feedstock, and the reaction time is from about 0.5, preferably from about 2, to about 10, preferably to about 6 hours. If the isomerization is performed on a continuous basis, the space velocity is in the range of from about 0.1, preferably from about 0.5 to about 20, preferably to about 10 parts of dimethylnaphthalene feedstock per part of zeolite component of the catalyst by weight per hour.

For each of the cyclization, dehydrogenation, and isomerization reactions described hereinabove, it is preferable to conduct each reaction at the lowest possible reaction temperature that provides for the conversion of a significant portion of the reaction feedstock to the respective product. At elevated reaction temperatures, coke, tars and other reaction sideproducts tend to form more rapidly and deposit on and deactivate the catalysts disclosed herein. However, regardless of the reaction temperature used, as the catalyst ages catalytic activity typically decreases. This decrease in catalyst activity, which results in reduced feedstock conversion at preselected reaction conditions such as reaction pressure, catalyst level, space velocity and reaction temperature, can be offset somewhat by increasing the reaction temperature. Consequently, a preferred procedure for maximizing the useful life of the cyclization, dehydrogenation and isomerization catalysts of this invention is to begin using the catalysts at as low a reaction temperature that provides for the conversion of a significant portion of the respective feedstock and then increase the temperature of the reaction as the catalyst ages so as to maintain desirable feedstock conversion levels. For example, when using a batch process, the temperature of the reaction can be raised with each successive batch. When using a continuous process, the reaction temperature of the catalyst bed or continuous stirred tank reactor can be raised as the catalyst ages. When using an aged, i.e., partially deactivated, cyclization catalyst in the method of this invention, a reaction temperature greater than 250° C. is suitable for maintaining the conversion of a significant portion and preferably at least about 50 wt % and more preferably at least about 70 wt % of the cyclization reaction feedstock to the desired product or products. Preferably this temperature is in the range of from about 255° C. to about 400° C. and more preferably in the range of from about 260° C. to about 320° C. Cyclization catalysts of this invention may also be reactivated by raising the reaction temperature for a period of time, then returning to the original reaction temperature. When employing an aged dehydrogenation catalyst in the method of this invention, a reaction temperature greater than 300° C. is suitable for maintaining the conversion of a significant portion and preferably at least about 50 wt % and more preferably at least about 70 wt % of the dehydrogenation reaction feedstock to the desired product or products. Preferably this temperature is in the range of from about 305° C. to about 500° C., and more preferably in the range of from about 310° C. to about 450° C. When using an aged isomerization catalyst in the method of this invention, a reaction temperature greater than 300° C. is suitable for maintaining the conversion of a significant portion and preferably at least about 20 wt % of the isomerization reaction feedstock to the desired product or products. Preferably this temperature is in the range of from about 305° C. to about 420° C., more preferably in the range of from about 310° C. to about 380° C.

The following U.S. Patent applications are hereby specifically incorporated by reference:

U.S. Ser. No. 316,308 filed on Feb. 27. 1989
U.S. Ser. No. 539,007 filed on Jun. 15, 1990
U.S. Ser. No. 539,087 filed on Jun. 15. 1990
U.S. Ser. No. 556,297 filed on Jul. 20, 1990.

The present invention will be more clearly understood from the following specific examples.

EXAMPLES 1-8

In each of Examples 1-8, 20-1000 grams of an alkenyl-benzene were introduced into a stirred glass reactor, and dry nitrogen gas was employed to continuously purge the reaction medium to preclude moisture therefrom. The alkenylbenzene employed was 5-(o-tolyl)-pentene-2 in Examples 1-6, 5-(p-tolyl)-pentene-2 in Example 7 and 4-phenyl-pentene-2 in Example 8. Unsupported ultrastable Y-type crystalline aluminosilicate molecular sieve catalyst (Union Carbide's LZ-Y72) having a unit cell size of 24.51 Angstroms and containing 2.5 weight percent of sodium (calculated as sodium oxide) was added slowly to the alkenylbenzene in the reactor at a temperature below commencement of the cyclization of the alkenylbenzene. The catalyst was in the form of an unsupported powder in Examples 1-4, 7 and 8, and in the form of pellets containing 80 weight percent of the same sieve supported on 20 weight percent of an alumina support in Examples 5 and 6. The catalyst was maintained under dry, moisture-free conditions prior to use in Examples 1-3 and 5-8 but was allowed to adsorb moisture from air saturated with moisture at 30°-60° C. in Example 4. The catalyst employed in Example 4 contained 10-20 weight percent of water.

The temperature of the reaction medium was then raised quickly to the desired reaction temperature. Samples of the resulting reaction product were withdrawn from the reactor at various reaction times and analyzed to monitor the reaction. The desired cyclized product was 1,5-dimethyltetralin in Examples 1-6, 1,7-dimethyltetralin in Example 7 and 1,4-dimethyltetralin in Example 8. The experimental conditions employed, the compositions of the feedstock employed and of the resulting products containing up to 13 carbon atoms and the percent conversion of the alkenylbenzene feedstock, and the percent selectivity of the formation of desired product from the total amount of alkenylbenzene converted for each of Examples 1-8 are presented in Table 1. For the calculation of this percent selectivity, the desired product is the sum of 1,5-dimethyltetralin and 1,5-dimethylnaphthalene in Examples 1-6, the sum of 1,7-dimethyltetralin and 1,7-dimethylnaphthalene in Example 7, and the sum of 1,4-dimethyltetralin and 1,4-dimethylnaphthalene in Example 8.

Comparison of the results of Examples 2 and 4 illustrates that, even at the low feed-to-catalyst weight ratio employed in Example 4, the presence of a large concentration of water therein resulted in substantially reduced percents conversion, even after a reaction time of about 12 hours.

TABLE 1

| Reaction Conditions | Example 1 | | | Example 2 | | | Example 3 | | Example 4 | | |
|---|---|---|---|---|---|---|---|---|---|---|---|
| | Feed-stock | Product | | Feed-stock | Product | | Feed-stock | Product | Feed-stock | Product | |
| Reaction time (hrs) | 0 | 4 | 6 | 0 | 3 | 6.8 | 0 | 0.5 | 0 | 6.8 | 12.8 |
| Temperature (°C.) | | 148 | 148 | | 168 | 168 | | 243 | | 170 | 170 |
| Pressure (psig) | | 1.0 | 1.0 | | 1.0 | 1.0 | | 1.0 | | 0.0 | 0.0 |
| Feed/Catalyst (wt.) | | 50.1 | 50.1 | | 50.1 | 50.1 | | 49.9 | | 43.5 | 43.5 |
| Composition (wt. %) | | | | | | | | | | | |
| Aryl-pentene feed | 98.6 | 3.4 | 1.1 | 98.6 | 1.7 | 0 | 93.6 | 0 | 96.1 | 68.3 | 52.5 |
| Solvent | 0.1 | 0.6 | 0.4 | 0.1 | 0 | 0 | 0 | 0.7 | 0.3 | 0.0 | 0.0 |

TABLE 1-continued

| Desired Product | | | | | | | | | | | |
|---|---|---|---|---|---|---|---|---|---|---|---|
| 1,5-DMT | | 89.2 | 92.5 | | 91.2 | 93.5 | 4.1 | 86.2 | 1.1 | 26.8 | 41.0 |
| 1,5-DMN | | 0 | 0 | | 0.5 | 1.2 | 0.1 | 2.3 | 0 | 0.1 | 0.3 |
| By-Products | | | | | | | | | | | |
| Intermediate | | 3.2 | 2.5 | | 2.5 | 0 | 0 | 0 | 0.3 | 2.0 | 2.9 |
| DMT isomers | 0 | 0.4 | 0.4 | 0 | 0.6 | 0.6 | 0.1 | 1.4 | 0.0 | 0.4 | 0.6 |
| Aryl-pentane | 0.2 | 0.3 | 0.5 | 0.2 | 0.9 | 2.0 | 0.3 | 4.4 | 0.4 | 0.2 | 0.1 |
| 1,4-DMN | | 0 | 0 | | 0 | 0 | 0 | 0 | | 0.0 | 0.0 |
| 1,7-DMN | | 0 | 0 | | 0 | 0 | 0 | 0 | | 0.0 | 0.0 |
| Lights | 0.1 | 1.3 | 1.0 | 0.1 | 0.1 | 0 | 0.2 | 1.5 | 0.5 | 0.4 | 0.5 |
| Heavies | 0 | 0 | 0 | 0 | 0.3 | 0.4 | 0 | 0.1 | 0.0 | 0.0 | 0.0 |
| Other | 1.0 | 1.5 | 1.5 | 1.0 | 2.3 | 2.2 | 1.5 | 3.2 | 1.4 | 1.5 | 2.0 |
| Total | 100.0 | 99.9 | 100.0 | 100.0 | 100.0 | 100.0 | 99.9 | 99.8 | 100.0 | 99.8 | 99.9 |
| % Conversion | | 96.6 | 98.9 | | 98.3 | 100.0 | | 100.0 | | 28.9 | 45.4 |
| % Selectivity | | 93.7 | 94.9 | | 94.6 | 96.0 | | 90.2 | | 92.8 | 94.6 |

| Reaction Conditions | Example 5 | | Example 6 | | Example 7 | | Example 8 | |
|---|---|---|---|---|---|---|---|---|
| | Feedstock | Product | Feedstock | Product | Feedstock | Product | Feedstock | Product |
| Reaction time (hrs) | 0 | 4 | 0 | 11 | 0 | 8.5 | 0 | 3 |
| Temperature (°C.) | | 171 | | 201 | | 170 | | 170 |
| Pressure (psig) | | 0.0 | | 0.0 | | 1.0 | | 1.0 |
| Feed/Catalyst (wt.) | | 8.3 | | 40.0 | | 51.0 | | 56.0 |
| Composition (wt. %) | | | | | | | | |
| Aryl-pentene feed | 97.6 | 0.0 | 97.6 | 5.2 | 99.9 | 3.3 | 98.3 | 0.5 |
| Solvent | 0.9 | 0.1 | 0.9 | 0.0 | 0.0 | | 0.8 | 0.0 |
| Desired Products | | | | | | | | |
| 1,5-DMT | 0.0 | 84.1 | 0.0 | 75.6 | | 90.0 | | 92.7 |
| 1,5-DMN | | 2.2 | 0.0 | 0.0 | | 0.0 | | 0.0 |
| By-Products | | | | | | | | |
| Intermediate | 0.2 | 0.0 | 0.2 | 0.3 | | | | |
| DMT isomers | 0.1 | 1.2 | 0.1 | 1.3 | | 1.3 | | |
| Aryl-pentane | 0.1 | 4.0 | 0.1 | 3.9 | | 2.9 | | 2.5 |
| 1,4-DMN | | 0.0 | | 0.0 | | 0.0 | | 1.6 |
| 1,7-DMN | | 0.0 | | 2.4 | | 1.5 | | 0.0 |
| Lights | 0.0 | 0.1 | 0.0 | 0.1 | | | | |
| Heavies | 0.0 | 0.4 | 0.0 | 0.3 | | | | |
| Other | 0.0 | 7.5 | 0.9 | 10.8 | 1.1 | 1.0 | 1.0 | 2.8 |
| Total | 99.7 | 99.7 | 99.7 | 99.9 | 100.0 | 100.0 | 100.0 | 100.0 |
| % Conversion | | 100.0 | | 94.7 | | 96.6 | | 99.5 |
| % Selectivity | | 88.5 | | 84.4 | | 95.7 | | 96.4 |

EXAMPLES 9–23

In each of Examples 9–23, a cyclization catalyst was packed into a stainless steel reactor, and the reactor was immersed into a fluidized sand bath at the desired reaction temperature. A mixture of 5-o-tolyl-2-pentene in the liquid phase and nitrogen was passed continuously through the reactor. At least once during at least one catalyst cycle, the resulting product stream was sampled and analyzed. The experimental conditions employed, the compositions of the feedstock employed and of the resulting products containing up to 13 carbon atoms, the percent conversion of the alkenylbenzene feedstock, and the percent selectivity of the formation of desired product from the total amount of alkenylbenzene converted in each of Examples 9–23 are presented in Table 2.

A catalyst cycle was concluded by discontinuing the flow of the 5-o-tolyl-2-pentene into the reactor and then purging the reactor at the reaction temperature with nitrogen to remove the hydrocarbons. The reactor was next heated to 500° C. and purged with air until the carbon dioxide content of the reactor effluent was less than 0.1 weight percent. This procedure resulted in the regeneration of the catalyst. The reactor was then cooled to the desired reaction temperature, and then the mixture of 5-o-tolyl-2-pentene in the liquid phase and nitrogen was passed continuously into the reactor.

In each of Examples 9–12 and 19–23, the reactor had an outside diameter of 0.25 inch, an inside diameter of 0.18 inch, a length of 5.5 inches, and one gram of the catalyst was packed into the reactor. In each of Examples 13–18, the reactor had an outside diameter of 0.375 inch, an inside diameter of 0.28 inch, a length of 5 inches, and 2.5 grams of the catalyst were packed into the reactor.

In each of Examples 9–14, an unsupported ultra-stable Y-sieve containing platinum and copper components was employed. This catalyst was prepared by adding to 30 grams of the commercial ultra-stable Y-sieve (Union Carbide's LZ-Y20) 15 milliliters of distilled water and 30 grams of an aqueous solution containing 1 weight percent $H_2PtCl_6.6H_2O$, calculated as platinum, and 2 weight percent of copper in the form of cupric nitrate and calculated as elemental copper. The resulting slurry was mixed until it was uniform and then dried. The resulting solid was calcined at 500° C. in air for 4 hours, crushed and screened to obtain 0.0164–0.0278 inch (24–40 mesh) particles.

In each of Examples 15–18, a supported ultra-stable Y-sieve containing platinum and copper components was employed. This catalyst was prepared by crushing and screening a commercial sample of particles containing 80 weight percent of Union Carbide's LZ-Y20 supported on 20 weight percent of alumina to yield particles in the range of 24–40 mesh. To 10 grams of the supported sieve was added 11 milliliters of 0.9 weight percent $H_2PtCl_6$, calculated as platinum, and 1.8 weight percent of copper in the form of cupric nitrate, calculated as elemental copper. The resulting slurry was mixed until it was uniform and then dried. The resulting solid was calcined at 500° C. in air for 4 hours.

Each of Examples 19–23 was performed using the apparatus and procedure of Examples 9–12 at a reaction temperature of 154° C. and a space velocity of 1.1. The diluent gas was helium in Examples 19 and 20, hydrogen in Examples 21 and 22 and nitrogen in Example 23. The molar ratio of diluent-to-5-o-tolyl-2-pentene was 1.3 in Example 19 and 2.1 in each of Examples 20-23. The catalyst was unsupported in each example, and was ultra-stable Y-sieve (Union Carbide's LZ-Y20) in Example 19, ultra-stable Y-sieve containing 2 weight percent of copper in the form of cupric nitrate, (calculated as elemental copper) in each of Examples 20 and 21, ultra-stable Y-sieve treated with $SiCl_4$ in Example 22 and ultra-stable Y-sieve containing 2 weight percent of copper in the form of cupric nitrate (calculated as elemental copper) and 1 weight percent of platinum in the form of $H_2PtCl_6$. (calculated as elemental platinum) in Example 23. In each of Examples 19-23, samples of the product stream were taken at several times after the beginning of the catalyst cycle and analyzed. From these measurements the yields of 1,5-dimethyltetralin were calculated and in FIG. 1 are plotted versus the number of hours since the respective catalyst had been regenerated.

The results indicate that the addition of copper to the sieve or the treatment of the sieve with silicon tetrachloride improves the selectivity of the catalyst but that the catalytic activity decreases with time. However, the addition of both platinum and copper to the sieve affords both substantially improved selectivity and excellent catalyst activity maintenance.

TABLE 2

| Reaction Conditions | Feed | Example 9 | Example 10 | Example 11 | Example 12 |
|---|---|---|---|---|---|
| Hours on stream since regeneration | | 62.5 | 69.0 | 186.5 | 192.75 |
| Catalyst cycle no. | | 1 | 2 | 2 | 2 |
| Temperature (°C.) | | 154 | 153 | 153 | 204 |
| Pressure (psig) | | 73.5 | 19.5 | 32.5 | 53.5 |
| Space velocity (wt. feed/wt. catalyst/hour) | | 1.07 | 1.08 | 2.20 | 2.20 |
| Composition (wt. %) Feed | | | | | |
| Aryl-pentene | 97.80 | 0.04 | 0.02 | 6.81 | 0.93 |
| Diluent/Aryl-pentene mole ratio | | 2.16 | 2.26 | 2.22 | 2.22 |
| Desired Products | | | | | |
| 1,5-DMT | 0.0 | 83.99 | 94.36 | 87.02 | 84.53 |
| 1,5-DMN | 0.0 | 2.54 | 0.95 | 0.10 | 4.18 |
| By-Products | | | | | |
| Intermediate | 0.11 | 0.00 | 0.00 | 3.02 | 0.36 |
| DMT isomers | 0.11 | 0.39 | 0.03 | 0.55 | 0.86 |
| DMN isomers | 0.0 | 0.11 | 0.00 | 0.05 | 0.41 |
| Aryl-pentane | 0.17 | 8.76 | 1.61 | 0.32 | 3.67 |
| Totals | 98.2 | 95.8 | 96.9 | 97.8 | 94.9 |
| % Conversion | | 99.9 | 99.9 | 93.0 | 99.0 |
| % Selectivity | | 88.5 | 97.5 | 95.7 | 91.6 |

| Reaction Conditions | Feed | Example 13 | Example 14 |
|---|---|---|---|
| Hours on stream since regeneration | | 167 | 421.75 |
| Catalyst cycle no. | | 5 | 5 |
| Temperature (°C.) | | 153 | 153 |
| Pressure (psig) | | 3 | 11 |
| Space velocity (wt. feed/wt. catalyst/hour) | | 1.14 | 1.25 |
| Composition (wt. %) Feed | | | |
| Aryl-pentene | 97.28 | 0.00 | 0.02 |
| Diluent/Aryl-pentene mole ratio | | 2.69 | 0.44 |
| Desired Products | | | |
| 1,5-DMT | 0.00 | 94.45 | 94.48 |
| 1,5-DMN | 0.00 | 0.26 | 0.35 |
| By-Products | | | |
| Intermediate | 0.32 | 0.47 | 0.13 |
| DMT isomers | 0.25 | 0.03 | 0.30 |
| DMN isomers | 0.00 | 0.00 | 0.02 |
| Aryl-pentane | 0.01 | 2.55 | 2.15 |
| Totals | 97.9 | 97.8 | 97.5 |
| % Conversion | | 100 | 100 |
| % Selectivity | | 97.4 | 97.5 |

| Reaction Conditions | Feed | Example 15 | Example 16 | Example 17 | Example 18 |
|---|---|---|---|---|---|
| Hours on stream since regeneration | | 15.00 | 10.50 | 162.25 | 306.27 |
| Catalyst cycle no. | | 1 | 2 | 5 | 5 |
| Temperature (°C.) | | 152 | 154 | 153 | 163 |
| Pressure (psig) | | 2 | 2 | 2 | 2 |
| Space velocity (wt. feed/wt. catalyst/hour) | | 1.20 | 1.22 | 1.20 | 1.23 |
| Composition (wt. %) Feed | | | | | |
| Aryl-pentene | 98.30 | 1.01 | 0.00 | 0.00 | 0.00 |
| Diluent/Aryl-pentene mole ratio | | 2.53 | 2.49 | 2.13 | 2.15 |
| Desired Products | | | | | |
| 1,5-DMT | 0.00 | 81.97 | 93.14 | 95.18 | 94.79 |
| 1,5-DMN | 0.00 | 1.59 | 1.88 | 0.70 | 0.68 |
| By-Products | | | | | |
| Intermediate | 0.31 | 1.31 | 0.00 | 0.00 | 0.00 |
| DMT isomers | 0.17 | 1.53 | 0.39 | 0.32 | 0.42 |
| DMN isomers | 0.00 | 0.00 | 0.00 | 0.00 | 0.00 |
| Aryl-Pentane | 0.10 | 10.47 | 2.69 | 2.10 | 2.33 |
| Totals | 98.9 | 97.9 | 98.1 | 98.3 | 98.2 |
| % Conversion | | 99.0 | 100.0 | 100.0 | 100.0 |
| % Selectivity | | 85.9 | 96.7 | 97.5 | 97.1 |

EXAMPLES 24-29

In each of Examples 24-29, the liquid feed and a 5 weight percent palladium-on-carbon catalyst were charged to a flask and nitrogen was continuously passed through the reaction mixture to remove oxygen. The temperature of the reaction mixture was raised to the reaction temperature, and periodically samples were removed from the flask and analyzed. Hydrogen generated by the reaction was permitted to vent from the flask during the reaction. The experimental conditions employed, the compositions of the feedstock employed and of the resulting products containing up to 13 carbon atoms, the percent conversion of the feedstock, and the percent selectivity of the formation of desired product from the total amount of feedstock converted in each of Examples 24-29 are presented in Table 3.

The results in Table 3 illustrate that even with the mild temperature and pressure conditions employed in Examples 24-29, the dehydrogenation of the method of this invention affords both excellent conversion and selectivity.

TABLE 3

| Conditions | Feed | Example 24 | Example 25 | Feed | Ex. 26 | Feed | Ex. 27 | Feed | Ex. 28 | Feed | Ex. 29 |
|---|---|---|---|---|---|---|---|---|---|---|---|
| Hours on stream | | 2.0 | 4.8 | 6.0 | 8.3 | | 8.5 | | 3.0 | 3.0 | 6.3 |
| Catalyst cycle no. | | 1 | 1 | 1 | 1 | | 1 | | 1 | | 1 |
| Temperature (°C.) | | 242 | 243 | 245 | 244 | | 251 | | 253 | | 254 | 254 |
| Pressure (psig) | | 1.0 | 1.0 | 1.0 | 1.0 | | 0.0 | | 0.0 | | 0.0 | 1.0 |
| Feed/catalyst weight ratio | | 10.0 | 10.0 | 50.0 | 50.0 | | 100.0 | | 49.9 | | 100.0 | 10.0 |

TABLE 3-continued

| Conditions | Feed | Example 24 | | Example 25 | | Feed | Ex. 26 | Feed | Ex. 27 | Feed | Ex. 28 | Feed | Ex. 29 |
|---|---|---|---|---|---|---|---|---|---|---|---|---|---|
| Compositions (wt. %) | | | | | | | | | | | | | |
| 1,4-DMT | 0.0 | 0.0 | 0.0 | 0.0 | 0.0 | | | | | 92.7 | | | |
| 1,5-DMT | 92.0 | 2.2 | 0.0 | 4.2 | 1.9 | 93.9 | 1.1 | 0.5 | | | | 1.2 | 0.0 |
| 1,6-DMT | 0.0 | 0.0 | 0.0 | 0.0 | 0.0 | 0.6 | | 0.8 | | | | 55.2 | 0.0 |
| 1,7-DMT | 0.0 | 0.0 | 0.0 | 0.0 | 0.0 | | | 89.4 | 0.4 | | | | |
| 1,8-DMT | 0.0 | 0.0 | 0.0 | 0.0 | 0.0 | | | | | | | 36.0 | 1.4 |
| other DMTs | 0.1 | 0.4 | 0.2 | 0.3 | 0.0 | 1.2 | 0.3 | 0.1 | 0.0 | 0.0 | 3.6 | 1.0 | 0.0 |
| m-xylene | 0.1 | 0.6 | 0.5 | 0.5 | 0.3 | 0.1 | 0.3 | 0.0 | 0.0 | | | | 0.4 |
| non-cyclic | 4.9 | 4.5 | 3.9 | 4.3 | 4.3 | 2.8 | 1.7 | 7.5 | 6.7 | 5.3 | 5.0 | 3.7 | 2.2 |
| Products | | | | | | | | | | | | | |
| 1,3-DMN | 0.0 | 0.0 | 0.0 | 0.0 | 0.0 | | 0.0 | 0.0 | 0.0 | 0.2 | 0.6 | | 0.0 |
| 1,4-DMN | 0.0 | 0.0 | 0.0 | 0.0 | 0.0 | | 0.0 | 0.0 | 0.2 | 1.6 | 90.2 | | 0.0 |
| 1,5-DMN | 0.9 | 89.8 | 93.2 | 88.4 | 92.5 | 0.7 | 94.3 | 0.0 | 0.5 | | | | 1.3 |
| 1,6-DMN | 0.0 | 0.5 | 0.5 | 0.4 | 0.0 | | 0.8 | 0.0 | 0.8 | | | 0.9 | 58.2 |
| 1,7-DMN | 0.0 | 0.0 | 0.0 | 0.0 | 0.0 | | 0.1 | 1.5 | 90.5 | | | | 0.6 |
| 1,8-DMN | 0.0 | 0.0 | 0.6 | 0.2 | 0.0 | | 0.4 | 0.0 | 0.1 | | | | 35.6 |
| 2,6- + 2,7-DMNs | 0.0 | 0.0 | 0.0 | 0.0 | 0.0 | | 0.0 | 0.0 | 0.3 | | | | 0.2 |
| Lights | 0.1 | 1.5 | 1.0 | 1.1 | 0.6 | | 0.7 | 0.0 | 0.1 | 0.4 | | | 0.3 |
| Heavies | 0.1 | 0.0 | 0.0 | 0.0 | 0.0 | | 0.0 | 0.0 | 0.0 | | | 1.8 | 0.0 |
| Other | 1.8 | 0.5 | 0.1 | 0.5 | 0.4 | 0.6 | 0.4 | 0.0 | 0.2 | | 0.3 | | 0.0 |
| Total | 100.0 | 100.0 | 100.0 | 100.0 | 100.0 | 100.0 | 100.0 | 99.9 | 99.9 | 100.2 | 100.0 | 99.7 | 100.1 |
| Total DMNs | | 90.3 | 94.3 | 89.0 | 92.5 | | 95.5 | 1.5 | 92.4 | | 90.8 | | 95.8 |
| % Conversion | | 97.6 | 100.0 | 95.4 | 98.0 | | 98.8 | | 99.5 | | 99.5 | | 98.5 |
| % Selectivity | | 99 | 100 | 100 | 101 | | 101 | | 100 | | 96.0 | | 103.4 |

EXAMPLES 30-47

In each of Examples 30-47, the particular isomer of dimethylnaphthalene employed as the feed was mixed in liquid form with unsupported catalyst in a stirred reaction vessel with a continuous nitrogen purge to preclude oxygen from the system. The temperature of the reaction vessel was raised to the reaction temperature and samples were withdrawn at various times after commencement of the reaction and analyzed. The conditions employed, the compositions of the feedstock employed and of the resulting products containing up to 13 carbon atoms, the percent conversion of the feedstock, and the percent selectivity of the formation of desired product from the total amount of feedstock converted in each of Examples 30-47 are presented in Table 4.

The catalyst employed in Example 30 was a crystalline borosilicate molecular sieve (HAMS-1B from Amoco Chemical). The catalyst employed in Example 31 was Union Carbide's LZ-Y20 ultra-stable Y-type sieve, containing 2 weight percent of copper, calculated as elemental copper. The catalyst employed in Example 32 was Union Carbide's LZ-Y62, a non-ultra-stable, Y-type sieve in the ammonia-exchanged form and having a unit cell size of 24.73A. The catalyst employed in Examples 33 and 34 was commercially available Union Carbide's LZ-Y82, an ultra-stable molecular sieve having a unit cell size of 24.56A and a sodium content of less than 0.2 weight percent. In Example 33, the sieve was in the ammonia form and had not been calcined. In Example 34, the sieve had been calcined to form the hydrogen form. The catalyst employed in Example 35 was a commercially available amophous silica-alumina containing 13 weight percent of alumina. The catalyst employed in Example 36 was commercially available mordenite in the acid form. The catalyst employed in Examples 37, 38, 40-45 was commercially available Union Carbide's LZ-Y72 in the hydrogen form as received from the manufacturer. The catalyst employed in Example 39 was commercially available Grace USY sieve containing 2.6 weight percent of sodium and has chemical and physical properties that are very similar to those of Union Carbide's LZ-Y72, and is also suitable for use as a catalyst in either the cyclization or isomerization step in the method of this invention. 1,5-dimethylnaphthalene was the feed in Examples 30-44. The feed was 1,7-dimethylnaphthalene in Example 45 and 1,4-dimethylnaphthalene in Examples 46-47. For the purposes of Table 4, the concentration of 2,7-DMN in the product is taken to be approximately equal to the concentration of 1,7-DMN and is substracted from the sum of 2,6-DMN and 2,7-DMN (which are determined together) for the purpose of determining the concentration of 2,6-DMN alone. The effective maximum concentrations of a particular desired DMN in its triad is its equilibrium concentration in the triad, which generally is 40-45 weight percent.

TABLE 4

| Conditions | Feed | Ex. 30 | Feed | Ex. 31 | Feed | Ex. 32 | Ex. 33 | Ex. 34 | Ex. 35 | Ex. 36 |
|---|---|---|---|---|---|---|---|---|---|---|
| Temperature (°C.) | | 249 | | 243 | | 248 | 249 | 240 | 233 | 248 |
| Pressure (psig) | | 1 | | 1 | | 1 | 1 | 1 | 1 | 1 |
| Catalyst | | Amsac-3400 | | LZ-20 2% Cu | | LZ-Y62 | YZ-Y82[1] | LZ-Y82 | SiO$_2$/Al$_2$O$_3$[3] | Mordenite[4] |
| Feed/Catalyst wt. ratio | | 10 | | 10 | | 10.0 | 9.9 | 9.8 | 10.1 | 9.8 |
| Hours on stream | | 7.3 | | 13 | | 12 | 11.8 | 5.5 | 13 | 11.5 |
| Product Compositions (wt. %) | | | | | | | | | | |
| 1,2-DMN | | 0.0 | 0.0 | 0.0 | 0.1 | 0.0 | 0.0 | 0.0 | 0.4 | 0.0 | 0.0 |
| 1,3-DMN | | 0.0 | 0.0 | 0.0 | 0.0 | 0.0 | 0.0 | 0.0 | 0.0 | 0.0 | 0.0 |
| 1,4-DMN | | 0.0 | 0.0 | 0.0 | 0.0 | 0.0 | 0.0 | 0.0 | 0.0 | 0.0 | 0.0 |
| 1,5-DMN | | 93.4 | 69.3 | 82.6 | 8.7 | 82.6 | 82.3 | 75.6 | 4.1 | 21.9 | 41.2 |
| 1,6-DMN | | 0.0 | 20.1 | 11.8 | 37.8 | 11.8 | 12.1 | 18.3 | 25.4 | 42.8 | 29.4 |
| 1,7-DMN | | 0.0 | 0.0 | 1.2 | 1.5 | 1.2 | 1.3 | 1.2 | 3.6 | 1.2 | 0.7 |
| 2,3-DMN | | | 0.0 | 0.0 | 0.0 | 0.0 | 0.0 | 0.0 | 1.2 | 0.0 | 0.0 |

TABLE 4-continued

|  |  |  |  |  |  |  |  |  |  |
|---|---|---|---|---|---|---|---|---|---|
| 2,6- + 2,7-DMNs | 0.0 | 5.4 | 1.8 | 36.3 | 1.8 | 2.1 | 3.2 | 30.4 | 29.3 | 27.6 |
| Lights | 6.3 | 2.6 | 1.7 | 1.4 | 1.7 | 1.8 | 1.2 | 1.3 | 1.2 | 1.0 |
| Heavies | 0.0 | 1.9 | 0.2 | 5.8 | 0.2 | 0.1 | 0.1 | 16.2 | 1.2 | 0.0 |
| Naphthalene | 0.0 | 0.0 | 0.0 | 0.1 | 0.0 | 0.0 | 0.0 | 0.7 | 0.0 | 0.0 |
| Methylnaphthalenes | 0.0 | 0.2 | 0.6 | 6.5 | 0.6 | 0.3 | 0.2 | 12.7 | 2.0 | 0.1 |
| Other | 0.2 | 0.5 | 0.0 | 1.9 | 0.0 | 0.0 | 0.0 | 3.9 | 0.5 | 0.0 |
| Total | 99.9 | 100.0 | 99.9 | 100.1 | 99.6 | 100.1 | 99.8 | 100.1 | 100.1 | 100.0 |
| Total DMNs | 93.4 | 94.8 | 97.3 | 84.4 | 97.3 | 97.8 | 98.3 | 65.1 | 95.2 | 98.9 |
| 2,7-DMN % |  |  |  |  |  |  |  |  |  |  |
| 2,6-DMN % in the 1,5-, 1,6- and 2,6-DMN triad | 0.0 | 5.7 | 0.6 | 42.8 | 0.6 | 0.9 | 2.1 | 47.7 | 30.3 | 27.6 |
| 2,6-DMN selectivity |  | 100 |  | 71.7 |  |  |  | 40.5 | 93.1 | >100 |

| Conditions | Ex. 37 | Ex. 38 | Ex. 39 | Ex. 40 | Ex. 41 | Ex. 42 | Ex. 43 | Ex. 44 |
|---|---|---|---|---|---|---|---|---|
| Temperature (°C.) | 226 | 227 | 252 | 251 | 248 | 248 | 249 | 248 |
| Pressure (psig) | 1 | 1 | 1 | 1 | 1 | 1 | 1 | 1 |
| Catalyst | LZY-72[1] | LZY-72 | US-Y[5] | LZY-72 | LZY-72 | LZY-72 | LZY-72 | LZY-72 |
| Feed/Catalyst wt. ratio | 50.4 | 50.4 | 50.8 | 50.6 | 50.6 | 50.6 | 50.6 | 50.6 |
| Hours on stream | 19.5 | 23.3 | 11.5 | 3.0 | 4.8 | 6.8 | 8.5 | 10.5 |
| Product Compositions (wt. %) |  |  |  |  |  |  |  |  |
| 1,2-DMN | 0.0 | 0.0 | 0.0 | 0.0 | 0.0 | 0.0 | 0.0 | 0.0 |
| 1,3-DMN | 0.0 | 0.0 | 0.0 | 0.0 | 0.0 | 0.0 | 0.0 | 0.0 |
| 1,4-DMN | 0.0 | 0.0 | 0.0 | 0.0 | 0.0 | 0.0 | 0.0 | 0.0 |
| 1,5-DMN | 24.0 | 21.3 | 17.5 | 20.9 | 15.1 | 12.2 | 9.6 | 8.7 |
| 1,6-DMN | 39.9 | 40.3 | 41.5 | 41.6 | 41.6 | 41.6 | 40.0 | 39.7 |
| 1,7-DMN | 1.0 | 0.9 | 1.0 | 0.9 | 1.0 | 1.0 | 1.2 | 1.2 |
| 2,3-DMN | 0.0 | 0.0 | 0.0 | 0.0 | 0.0 | 0.0 | 0.0 | 0.0 |
| 2,6- + 2,7-DMNs | 31.8 | 34.2 | 35.9 | 32.9 | 37.6 | 40.0 | 43.0 | 43.3 |
| Lights | 1.9 | 0.9 | 1.2 | 1.6 | 1.6 | 1.2 | 1.0 | 1.1 |
| Heavies | 0.9 | 1.1 | 1.0 | 0.8 | 1.1 | 1.6 | 2.1 | 2.2 |
| Naphthalene | 0.0 | 0.0 | 0.0 | 0.0 | 0.0 | 0.0 | 0.0 | 0.0 |
| Methylnaphthalenes | 1.0 | 1.1 | 1.3 | 1.1 | 1.5 | 1.7 | 2.6 | 2.8 |
| Other | 0.4 | 0.2 | 0.5 | 0.3 | 0.5 | 0.7 | 0.5 | 0.9 |
| Total | 100.9 | 100.0 | 99.9 | 100.1 | 100.0 | 100.0 | 100.0 | 99.9 |
| Total DMNs | 96.7 | 96.7 | 95.9 | 96.3 | 95.2 | 94.8 | 93.9 | 93.0 |
| 2,7-DMN % | 1.1 |  | 1.1 |  |  |  |  | 1.6 |
| 2,6-DMN % in the 1,5-, 1,6- and 2,6-DMN triad | 32.5 | 35.1 | 37.2 | 33.8 | 39.2 | 42.0 | 45.7 | 46.5 |
| 2,6-DMN selectivity | 99.5 | 99.9 | 97.3 | 98.4 | 95.6 | 94.6 | 92.3 | 90.5 |

Footnotes
[1] not calcined
[2] not calcined
[3] 13% Al$_2$O$_3$
[4] in H form
[5] ultra-stable sieve containing 2.6% Na

| Conditions | Feed | Ex. 45 | Feed | Ex. 46 | Ex. 47 |
|---|---|---|---|---|---|
| Temperature (°C.) |  | 251 |  | 247 | 252 |
| Pressure (psig) |  | 1 |  | 1 | 1 |
| Catalyst | LZY-72 | LZY-72 | LZY-72 | LZY-72 | LZY-72 |
| Feed/Catalyst wt. ratio |  | 50.0 |  | 44.0 | 44.0 |
| Hours on stream |  | 4.0 |  | 2.0 | 6.5 |
| Product Compositions (wt. %) |  |  |  |  |  |
| 1,2-DMN | 0.0 | 0.0 | 0.0 | 0.1 | 0.4 |
| 1,3-DMN | 0.0 | 0.0 | 0.6 | 50.8 | 51.0 |
| 1,4-DMN | 0.0 | 0.0 | 90.6 | 15.1 | 9.0 |
| 1,5-DMN | 0.5 | 0.2 | 0.0 | 0.0 | 0.0 |
| 1,6-DMN | 0.7 | 1.4 | 0.0 | 0.0 | 0.0 |
| 1,7-DMN | 90.4 | 40.5 | 0.0 | 0.0 | 0.1 |
| 2,3-DMN | 0.0 | 0.0 | 0.0 | 22.1 | 23.3 |
| 2,6-DMN | 0.0 | 1.3 | 0.0 | 0.0 | 0.3 |
| 2,7-DMN | 0.3 | 44.7 | 0.0 | 0.0 | 0.1 |
| Lights | 6.6 | 6.3 | 5.2 | 4.3 | 3.6 |
| Heavies | 0.0 | 0.7 | 0.0 | 1.8 | 3.8 |
| Naphthalene |  |  | 0.0 | 2.0 | 3.3 |
| Methylnaphthalenes | 0.2 | 1.7 | 3.6 | 3.9 | 4.8 |
| Other | 1.3 | 2.8 | 0.0 | 0.0 | 0.3 |
| Total | 100.0 | 99.6 | 100.0 | 100.1 | 100.0 |
| Total DMNs | 92.0 | 88.4 | 91.1 | 88.1 | 84.2 |
| % desired DMN[1] in its triad | 0.3 | 52.2 | 0.6 | 25.1 | 28.0 |
| Selectivity |  | 89.0 |  | 87.5 | 74.8 |

[1] 2,7-DMN in Example 45 and 2,3-DMN in Examples 46–47.

EXAMPLE 48

7.5 kilograms of distilled water, 7.5 kilograms of an aqueous solution containing 40 weight percent of tetraethylamine hydroxide, 50 grams of sodium hydroxide and 300 grams of sodium aluminate were stirred and dissolved in a 25-gallon stainless steel tank. The resulting solution and 12.2 kilograms of a silica sol containing 40 weight percent of silica were mixed and stirred in a 10-gallon autoclave at 150° C. for 72 hours. The resulting mixture was filtered, and the separated solids were washed three times with distilled water, dried at 120° C. and then calcined at 538° C. for 4 hours.

The resulting dried powder contained 0.37 weight percent of sodium, calculated as elemental sodium, and x-ray diffraction analysis indicated that the powder had the x-ray diffraction pattern of beta zeolite. The following is the x-ray diffraction pattern of the powder product, showing only the lines that are common to all 4 sources of beta zeolite in U.S. Pat. No. 3,308,069.

| Line d(A) | Relative Intensity |
|---|---|
| 4.18 | 16.2 |
| 3.99 | 100.0 |
| 3.54 | 6.1 |
| 3.35 | 12.6 |
| 3.11 | 3.0 |
| 3.05 | 14.6 |
| 2.94 | 5.3 |
| 2.69 | 4.1 |
| 2.54 | 1.5 |
| 2.08 | 11.5 |

The powder was employed as the catalyst without being ion-exchanged. Some powder was ion-exchanged using the procedure of Example 50 to reduce the sodium content, and after being ion-exchanged, the powder's alumina content, silica-to-alumina mole ratio and silicon-to-aluminum atom ratio were measured as 1.14 weight percent, 68:1 and 34:1, respectively.

EXAMPLE 49

8 kilograms of distilled water, 8 kilograms of an aqueous solution containing 40 weight percent of tetraethylamine hydroxide, 3.81 kilograms of an aqueous solution containing 20 weight percent of tetraethylamine hydroxide, 0.6 kilogram of sodium aluminate, and 12.2 kilograms of a silica sol containing 40 weight percent of silica were mixed and stirred in a 10-gallon autoclave at 150° C. for 72 hours. The resulting mixture was filtered, and the separated solids were washed three times with distilled water, added at 120° C. for about 16 hours and then calcined at 538° C. for 6 hours.

The resulting dried powder contained 0.17 weight percent of sodium, calculated as elemental sodium. X-ray diffraction analysis indicated that the powder had the x-ray diffraction pattern of beta zeolite. The following is the x-ray diffraction pattern of the powder product, showing only the lines that are common to all 4 sources of beta zeolite in U.S. Pat. No. 3,308,069.

| Line d(A) | Relative Intensity |
|---|---|
| 4.19 | 17.7 |
| 4.01 | 100.0 |
| 3.54 | Weak |
| 3.35 | 13.8 |
| 3.11 | Weak |
| 3.05 | 13.4 |
| 2.95 | 2.8 |
| 2.67 | Weak |
| 2.49 | 0.6 |
| 2.09 | 7.6 |

The powder was employed as the catalyst without being ion-exchanged. After being ion-exchanged using the procedure of Example 50 in order to reduce the sodium content, the powder's silica-to-alumina mole ratio and silicon-to-aluminum atom ratio were measured as 30:1 and 14.8:1, respectively.

EXAMPLE 50

2.3 kilograms of the un-ion-exchanged catalyst powder produced in Example 49, 4 kilograms of distilled water, and 12 kilograms of an aqueous solution containing 19 weight percent of ammonium nitrate were stirred in a 22-liter flask at 72° C. for 4 hours. The mixture was then cooled; the liquid was removed by decantation, and the resulting ion-exchanged catalyst was then washed with water. The catalyst was then dried at 120° C. and calcined at 538° C. for 3 hours. The ion-exchanged catalyst contained 0.01 weight percent of sodium (calculated as elemental sodium), 2.43 weight percent of aluminum (calculated as elemental aluminum), and a silica-to-alumina mole ratio and a silicon-to-aluminum atomic ratio of 30:1 and 14.8:1, respectively.

163 grams of this dry, ion-exchanged beta zeolite powder, 454 grams of an alumina sol containing 8.8 weight percent of solids, and 123 grams of distilled water were blended to obtain a smooth, uniform slurry. The slurry was maintained at 23° C. for 5 hours to permit liquid to evaporate from the slurry. The slurry was then dried at 120° C. for about 16 hours and calcined at 538° C. for 2 hours, to afford solids containing 80 weight percent of beta zeolite and 20 weight percent of alumina, which were then ground and sieved to form particles having a 20–40 mesh size.

EXAMPLES 51–69

In each of Examples 51–69, the particular feedstock employed was mixed in liquid form with unsupported catalyst in a stirred reaction vessel with a continuous nitrogen purge to preclude oxygen from the system. The weight ratio of the feedstock-to-zeolite component of the catalyst was 49:1 in each case. The pressure of the contents of the reaction vessel was maintained at about 1 pound per square inch gauge. The temperature of the reaction vessel was raised to the reaction temperature and samples were withdrawn at various times after commencement of the reaction and analyzed. The conditions employed, the compositions of the feedstock employed and of the resulting products, the percent of the 1,5-, 1,6- and 2,6-DMN triad in each thereof, the percent of 2,6-DMN in each such 1,5-, 1,6- and 2,6-DMN triad, the percent decreases in each 1,5-, 1,6- and 2,6-DMN triad, the percent gains in each 1,7-, 1,8- and 2,7-DMN triad and the percent gain in total methylnaphthalene and trimethylnaphthalene content in each of Examples 51–69 are presented in Tables 5–9.

The catalyst employed in Examples 51–53 was commercially available Union Carbide's unsupported LZ-Y72 in the hydrogen form as received from the manufacturer. The catalyst employed in Examples 54–57 was an unsupported beta zeolite having a relatively high silicon-to-aluminum ratio and prepared by the procedure of Example 48. The catalyst employed in Examples 58–66 was an unsupported beta zeolite having a relatively low silicon-to-aluminum ratio and prepared by the procedure of Example 49. A single sample of this catalyst was used for four cycles in Examples 61–66. The catalyst employed in Examples 67–69 was also the beta zeolite having the relatively low silicon-to-aluminum ratio and prepared by the procedure of Example 49, but in this instance ion-exchanged to reduce the sodium content and supported on an alumina matrix by the procedure of Example 50.

TABLE 5

| | Feed | Ex. 51 | Ex. 52 | Ex. 53 |
|---|---|---|---|---|
| Conditions | | | | |
| Catalyst | | LZ-Y72 | LZ-Y72 | LZ-Y72 |
| Temperature (°C.) | | 250 | 250 | 250 |
| Hours on Stream | | 1 | 3 | 4.75 |
| Product Composition (wt. %) | | | | |
| 1,5-DMN | 91.03 | 38.70 | 18.30 | 12.84 |
| 1,6-DMN | 3.73 | 36.92 | 40.67 | 40.35 |
| 2,6-DMN | 0 | 18.42 | 32.40 | 36.18 |
| 1,7-DMN | 0.74 | 0.81 | 0.93 | 1.08 |
| 2,7-DMN | 0 | 0.73 | 1.37 | 1.81 |
| Methylnaphthalenes | 0.06 | 0.62 | 1.43 | 2.03 |
| Trimethylnaphthalenes | 0.44 | 0.53 | 1.33 | 2.02 |
| Other | 4.00 | 3.27 | 3.57 | 3.69 |
| Total | 100.00 | 100.00 | 100.00 | 100.00 |
| 1,5-, 1,6- and 2,6-DMN triad content | 94.76 | 94.04 | 91.37 | 89.37 |
| 2,6-DMN percent in 1,5-, 1,6- and 2,6-DMN triad | 0 | 19.59 | 35.46 | 40.49 |
| 1,5-, 1,6- and 2,6-DMN triad percent loss | 0 | 0.72 | 3.39 | 5.39 |
| 1,7-, 1,8- and 2,7-DMN triad percent gain | 0 | 0.80 | 1.56 | 2.15 |
| Methylnaphthalene and trimethylnaphthalene percent gain | 0 | 0.71 | 2.32 | 3.61 |

TABLE 6

| | Feed | Ex. 54 | Ex. 55 | Ex. 56 | Ex. 57 |
|---|---|---|---|---|---|
| Conditions | | | | | |
| Catalyst from Example | | 48 | 48 | 48 | 48 |
| Temperature (°C.) | | 250 | 250 | 250 | 250 |
| Hours on Stream | | 1 | 3 | 5 | 7 |
| Product Composition (wt. %) | | | | | |
| 1,5-DMN | 91.03 | 54.00 | 28.93 | 18.94 | 14.09 |
| 1,6-DMN | 3.73 | 28.76 | 37.62 | 39.70 | 40.41 |
| 2,6-DMN | 0 | 0 | 12.91 | 28.63 | 35.96 |
| 1,7-DMN | 0.74 | 0.61 | 0.58 | 0.60 | 0.67 |
| 2,7-DMN | 0 | 0.67 | 1.09 | 1.13 | 1.28 |
| Methylnaphthalenes | 0.06 | 0.12 | 0.29 | 0.41 | 0.57 |
| Trimethylnaphthalenes | 0.44 | 0.10 | 0.19 | 0.34 | 0.46 |
| Other | 4.06 | 2.83 | 2.67 | 2.92 | 2.97 |
| Total | 100.00 | 100.00 | 100.00 | 100.00 | 100.00 |
| 1,5-, 1,6- and 2,6-DMN triad content | 94.76 | 95.67 | 95.18 | 94.60 | 94.05 |
| 2,6-DMN percent in 1,5-, 1,6- and 2,6-DMN triad | 0 | 13.49 | 30.08 | 38.01 | 42.05 |
| 1,5-, 1,6- and 2,6-DMN triad percent loss | 0 | −0.91 | −0.42 | 0.16 | 0.71 |
| 1,7-, 1,8- and 2,7-DMN triad percent gain | 0 | 0.54 | 0.93 | 0.99 | 1.21 |
| Methylnaphthalene and trimethylnaphthalene percent gain | 0 | −0.23 | 0.04 | 0.31 | 0.59 |

TABLE 7

| | Feed | Ex. 58 | Ex. 59 | Ex. 60 |
|---|---|---|---|---|
| Conditions | | | | |
| Catalyst from Example | | 49 | 49 | 49 |
| Temperature (°C.) | | 250 | 250 | 250 |
| Hours on Stream | | 1.25 | 3 | 5 |
| Product Composition (wt. %) | | | | |
| 1,5-DMN | 91.03 | 21.94 | 10.79 | 8.20 |
| 1,6-DMN | 3.73 | 38.62 | 40.89 | 41.20 |
| 2,6-DMN | 0 | 35.59 | 43.28 | 44.94 |
| 1,7-DMN | 0.74 | 0.52 | 0.60 | 0.64 |
| 2,7-DMN | 0 | 0.30 | 0.53 | 0.47 |
| Methylnaphthalenes | 0 | 0.33 | 0.59 | 0.84 |
| Trimethylnaphthalenes | 0.44 | 0.16 | 0.46 | 0.78 |
| Other | 4.06 | 2.54 | 2.86 | 2.93 |
| Total | 100.00 | 100.00 | 100.00 | 100.00 |
| 1,5-, 1,6- and 2,6-DMN triad content | 94.76 | 96.15 | 94.96 | 94.34 |
| 2,6-DMN percent in 1,5-, 1,6- and 2,6-DMN triad | 0 | 37.02 | 45.58 | 47.63 |
| 1,5-, 1,6- and 2,6-DMN triad percent loss | 0 | −1.39 | −0.20 | 0.42 |
| 1,7-, 1,8- and 2,7-DMN triad percent gain | 0 | 0.08 | 0.39 | 0.37 |
| Methylnaphthalene and trimethylnaphthalene percent gain | 0 | 0.05 | 0.61 | 1.18 |

TABLE 8

| | Feed | Ex. 61 | Ex. 62 | Ex 63 |
|---|---|---|---|---|
| Conditions | | | | |
| Catalyst from Example | | 49 | 49 | 49 |
| Temperature (°C.) | | 240 | 240 | 240 |
| Hours on Stream | | 3 | 3.9 | 3 |
| Catalyst Cycle | | 1st | 1st | 3rd |
| Product Composition (wt. %) | | | | |
| 1,5-DMN | 88.14 | 9.63 | 7.99 | 26.62 |
| 1,6-DMN | 3.66 | 39.45 | 39.53 | 35.39 |
| 2,6-DMN | 0 | 41.50 | 42.34 | 29.83 |
| 1,7-DMN | 0.74 | 0.66 | 0.69 | 0.57 |
| 2,7-DMN | 0 | 1.26 | 1.50 | 1.02 |
| Methylnaphthalenes | 0.13 | 0.99 | 1.17 | 0.26 |
| Trimethylnaphthalenes | 0.54 | 0.53 | 0.70 | 0.17 |
| Other | 6.79 | 5.98 | 6.08 | 6.14 |
| Total | 100.00 | 100.00 | 100.00 | 100.00 |
| 1,5-, 1,6- and 2,6-DMN triad content | 91.80 | 90.58 | 89.86 | 91.84 |
| 2,6-DMN percent in 1,5-, 1,6- and 2,6-DMN triad | 0 | 45.82 | 47.12 | 32.48 |
| 1,5-, 1,6- and 2,6-DMN triad percent loss | 0 | 1.22 | 1.94 | −0.04 |
| 1,7-, 1,8- and 2,7-DMN triad percent gain | 0 | 1.18 | 1.45 | 0.85 |
| Methylnaphthalene and trimethylnaphthalene percent gain | 0 | 0.85 | 1.20 | −0.24 |

| | Feed | Ex. 64 | Ex. 65 | Ex. 66 |
|---|---|---|---|---|
| Conditions | | | | |
| Catalyst from Example | | 49 | 49 | 49 |
| Temperature (°C.) | | 240 | 265 | 265 |
| Hours on Stream | | 45 | 3 | 4.5 |
| Catalyst Cycle | | 3rd | 4th | 4th |
| Product Composition (wt. %) | | | | |
| 1,5-DMN | 88.14 | 17.73 | 11.47 | 8.16 |
| 1,6-DMN | 3.66 | 38.10 | 39.23 | 39.73 |
| 2,6-DMN | 0 | 36.25 | 40.02 | 42.31 |
| 1,7-DMN | 0.74 | 0.59 | 0.66 | 0.72 |
| 2,7-DMN | 0 | 0.97 | 1.20 | 1.13 |
| Methylnaphthalenes | 0.13 | 0.33 | 0.48 | 0.70 |
| Trimethylnaphthalenes | 0.54 | 0.29 | 0.37 | 0.52 |
| Other | 6.79 | 5.74 | 6.57 | 6.73 |
| Total | 100.00 | 100.00 | 100.00 | 100.00 |
| 1,5-, 1,6- and 2,6-DMN triad content | 91.80 | 92.08 | 90.72 | 90.20 |
| 2,6-DMN percent in 1,5-, 1,6- and 2,6-DMN triad | 0 | 39.37 | 44.11 | 46.91 |
| 1,5-, 1,6- and 2,6-DMN triad percent loss | 0 | −0.28 | 1.08 | 1.60 |
| 1,7-, 1,8- and 2,7-DMN triad percent gain | 0 | 0.82 | 1.12 | 1.11 |
| Methylnaphthalene and trimethylnaphthalene percent gain | 0 | −0.05 | 0.18 | 0.55 |

TABLE 9

| | Feed | Ex. 67 | Ex. 68 | Ex. 69 |
|---|---|---|---|---|
| Conditions | | | | |
| Catalyst from Example | | 50 | 50 | 50 |
| Temperature (°C.) | | 250 | 250 | 250 |
| Hours on Stream | | 1 | 2 | 3 |
| Product Composition (wt. %) | | | | |
| 1,5-DMN | 88.14 | 16.50 | 11.20 | 9.23 |
| 1,6-DMN | 3.66 | 38.10 | 39.30 | 39.70 |
| 2,6-DMN | 0 | 37.42 | 41.07 | 42.15 |
| 1,7-DMN | 0.74 | 0.53 | 0.55 | 0.58 |
| 2,7-DMN | 0 | 0.97 | 0.84 | 1.00 |
| Methylnaphthalenes | 0.13 | 0.52 | 0.69 | 0.83 |
| Trimethylnaphthalenes | 0.54 | 0.32 | 0.62 | 0.75 |
| Other | 6.79 | 5.64 | 5.73 | 5.76 |
| Total | 100.00 | 100.00 | 100.00 | 100.00 |
| 1,5-, 1,6- and 2,6-DMN triad content | 91.80 | 92.02 | 91.57 | 91.08 |
| 2,6-DMN percent in 1,5-, 1,6- and 2,6-DMN triad | 0 | 40.67 | 44.85 | 46.28 |
| 1,5-, 1,6- and 2,6-DMN triad percent loss | 0 | −0.22 | 0.23 | 0.72 |
| 1,7-, 1,8- and 2,7-DMN triad percent gain | 0 | 0.76 | 0.65 | 0.84 |
| Methylnaphthalene and trimethylnaphthalene percent gain | 0 | 0.17 | 0.64 | 0.91 |

Comparison of the results in Tables 5–9 illustrates clearly that (1) the use of a beta zeolite catalyst affords reduced losses of the 1,5-, 1,6- and 2,6-dimethylnaphthalene triad, reduced formation of methylnaphthalenes, trimethylnaphthalenes and the 1,7-, 1,8- and 2,7-dimethylnaphthalene triad relative to the use of the LZ-Y72 zeolite catalyst; and (2) the use of a beta zeolite catalyst either unsupported or supported on a base material and having a relatively lower silicon-to-aluminum ratio affords greater formation of 2,6-dimethylnaphthalene and reduced losses of the 1,5-, 1,6- and 2,6-dimethylnaphthalene triad relative to the use of a beta zeolite catalyst having a relatively higher silicon-to-aluminum ratio and permits the use of lower reaction temperatures or the use at a higher temperature of even a partially deactivated catalyst relative to the use of a LZ-Y72 zeolite catalyst.

EXAMPLES 70–77

In each of Examples 70–77 a fixed bed reactor was used to evaluate a continuous process for the dehydrogenation of a feedstock containing 1,5-dimethyltetralin (1,5-DMT) to yield mainly 1,5-dimethylnaphthalene (1,5-DMN). The fixed bed reactor used was a 13 centimeter long stainless steel tube having a 0.20 centimeter inside diameter and packed with 3.15 grams of a catalyst containing 0.35 wt % platinum and 0.35 wt % rhenium on a 16-25 mesh gamma alumina support. Preheated feedstocks having the compositions shown in Tables 10 and 11 were pumped upflow through the catalyst bed in the reactor tube at the reaction conditions listed in Tables 10 and 11, respectively. Thermocouples installed in the reactor inlet and exit monitored the reaction temperature. Heating tape wrapped around the reactor tube was used to maintain the set reaction temperature. Reaction pressure was maintained to keep the feedstock and hydrocarbon products as liquids. Reactor effluent was collected in a 300 ml pressure vessel maintained at 70°–100° C. to keep the product mixture liquid. The hydrogen gas generated by the dehydrogenation reaction was vented continuously from the collection vessel through a pressure regulator.

The selectivity and conversion percentages presented in Tables 10 and 11 were calculated according to the following equations: (1,6-DMN is in the 1,5-, 1,6-, 2,6-DMN triad and can be isomerized to 2,6-DMN; consequently, 1,6-DMT and 1,6-DMN wt. percentages are included in the following equations.)

$$\% \text{ Selectivity} = \frac{[(\text{wt \% } 1,5 + 1,6\text{-}DMN \text{ in product}) - (\text{wt \% } 1,5 + 1,6\text{-}DMN \text{ in feed})] \times 100}{(\text{wt \% } 1,5 + 1,6\text{-}DMT \text{ in feed}) - (\text{wt \% } 1,5 + 1,6\text{-}DMT \text{ in product})}$$

$$\% \text{ Conversion} = \frac{[(\text{wt \% } 1,5 + 1,6\text{-}DMT \text{ in feed}) - (\text{wt \% } 1,5 + 1,6\text{-}DMT \text{ in product})] \times 100}{(\text{wt \% } 1,5 + 1,6\text{-}DMT \text{ in feed})}$$

Table 10 reports data for the single-pass conversion of the 1,5-DMT containing feedstock to 1,5-DMN containing product. Table 11 reports data for the single-pass conversion of a 1.5-DMT containing feedstock that was distilled to remove heavy components before subjecting the feedstock to the dehydrogenation reaction. Table 11 also reports data for a two-pass conversion of the 1,5-DMT containing feedstock. In the two-pass conversion procedure the product stream from the single-pass dehydrogenation reaction was collected and passed through the fixed bed dehydrogenation reactor a second time. This two-pass procedure simulates a process utilizing two or more fixed bed dehydrogenation reactors in series wherein the hydrogen formed by the dehydrogenation reaction is partially or totally vented between reactors.

TABLE 10

| | Feed | Ex. 70 | Ex. 71 | Ex. 72 |
|---|---|---|---|---|
| Condition | | | | |
| Hours on Stream | | 436 | 441 | 482 |
| Catalyst cycle no. | | 2 | 2 | 2 |
| Temperature (°C.) | | 401 | 400 | 400 |
| Pressure (psig) | | 201 | 201 | 202 |
| WHSV (grams feed/hr/gram catalyst) | | 4.14 | 2.07 | 0.54 |
| Composition (wt. %) | | | | |
| 1,5-DMT | 84.66 | 4.56 | 3.90 | 1.90 |
| 1,6-DMT | 0.91 | 0.07 | 0.12 | 0.21 |
| 2,6- + 2,7- + 1,7-DMT | 0.27 | 0.00 | 0.00 | 0.06 |
| 2,8-DMT | 0.68 | 0.31 | 0.16 | 0.00 |
| 2,5- + 1,8-DMT | 0.31 | 0.00 | 0.11 | 0.22 |
| Lights | 0.24 | 1.68 | 2.36 | 9.61 |
| C$_{12}$ Indane | 1.06 | 1.70 | 2.10 | 2.08 |
| o-Tolylpentane | 3.20 | 3.68 | 3.78 | 2.48 |
| Products | | | | |
| 1,5-DMN | 1.64 | 80.15 | 77.48 | 51.95 |
| 1,6-DMN | 0.07 | 2.37 | 4.18 | 11.20 |
| 1,7-DMN | 0.00 | 0.42 | 0.62 | 1.29 |
| 1,8-DMN | 0.00 | 0.18 | 0.11 | 0.04 |
| 2,6- + 2,7-DMN | 0.00 | 0.00 | 0.10 | 0.79 |
| 1-Methylnaphthalene | 0.00 | 0.57 | 1.15 | 7.60 |
| 2-Methylnaphthalene | 0.00 | 0.00 | 0.00 | 0.29 |
| Heavies | 6.69 | 3.38 | 2.23 | 2.08 |
| Others | 0.27 | 0.94 | 1.62 | 8.22 |
| Total | 100.00 | 100.00 | 100.00 | 100.00 |
| % Conversion | — | 94.6 | 95.3 | 97.5 |
| % Selectivity | — | 99.8 | 98.0 | 73.6 |

| | Ex. 73 | Ex. 74 | Ex. 75 |
|---|---|---|---|
| Conditions | | | |
| Hours on Stream | 503 | 957 | 1223 |
| Catalyst cycle no. | 2 | 2 | 2 |
| Temperature (°C.) | 401 | 400 | 400 |
| Pressure (psig) | 201 | 170 | 178 |
| WHSV (grams feed/hr/gram catalyst) | 1.07 | 2.12 | 2.13 |
| Composition (wt. %) | | | |

TABLE 10-continued

| | | | |
|---|---|---|---|
| 1,5-DMT | 3.51 | 3.17 | 7.59 |
| 1,6-DMT | 0.15 | 0.06 | 0.09 |
| 2,6- + 2,7- + 1,7-DMT | 0.00 | 0.00 | 0.00 |
| 2,8-DMT | 0.16 | 0.20 | 0.00 |
| 2,5- + 1,8-DMT | 0.00 | 0.08 | 0.23 |
| Lights | 3.31 | 2.05 | 1.54 |
| $C_{12}$ Indane | 2.56 | 1.82 | 1.78 |
| o-Tolylpentane | 3.74 | 3.78 | 3.77 |
| Products | | | |
| 1,5-DMN | 71.46 | 78.97 | 75.68 |
| 1,6-DMN | 6.54 | 3.72 | 3.09 |
| 1,7-DMN | 0.78 | 0.59 | 0.50 |
| 1,8-DMN | 0.04 | 0.05 | 0.18 |
| 2,6- + 2,7-DMN | 0.23 | 0.09 | 0.16 |
| 1-Methylnaphthalene | 2.09 | 0.79 | 0.65 |
| 2-Meothylnaphthalene | 0.10 | 0.06 | 0.05 |
| Heavies | 2.48 | 2.23 | 2.18 |
| Others | 2.85 | 2.33 | 2.52 |
| Total | 100.00 | 100.00 | 100.00 |
| % Conversion | 95.7 | 96.2 | 91.0 |
| % Selectivity | 93.1 | 98.3 | 98.9 |

TABLE 11

| | Feed | Ex. 76 (1st pass) | Ex. 77 (2nd pass) | Overall |
|---|---|---|---|---|
| Conditions | | | | |
| Hours on Stream | | 477 | 740 | |
| Catalyst cycle no. | | 3 | 3 | |
| Temperature (°C.) | | 400 | 401 | |
| Pressure (psig) | | 200 | 200 | |
| WHSV (grams feed/hr/gram catalyst) | | 4.30 | 4.36 | |
| Composition (wt. %) | | | | |
| 1,5-DMT | 83.16 | 7.78 | 1.05 | |
| 1,6-DMT | 2.79 | 0.20 | 0.04 | |
| 2,6- + 2,7- + 1,7-DMT | 0.87 | 0.06 | 0.00 | |
| 2,8-DMT | 0.82 | 0.45 | 0.06 | |
| 2,5- + 1,8-DMT | 0.87 | 0.20 | 0.05 | |
| Lights | 0.46 | 1.34 | 1.49 | |
| $C_{12}$ Indane | 1.52 | 1.71 | 1.65 | |
| o-Tolylpentane | 4.88 | 5.04 | 4.67 | |
| Products | | | | |
| 1,5-DMN | 2.02 | 76.00 | 79.30 | |
| 1,6-DMN | 0.36 | 4.51 | 7.17 | |
| 1,7-DMN | 0.03 | 0.88 | 1.24 | |
| 1,8-DMN | 0.01 | 0.17 | 0.12 | |
| 2,6- + 2,7-DMN | 0.08 | 0.18 | 0.33 | |
| 1-Methylnaphthalene | 0.00 | 0.28 | 1.19 | |
| 2-Methylnaphthalene | 0.06 | 0.01 | 0.05 | |
| Heavies | 0.17 | 0.45 | 0.80 | |
| Others | 1.70 | 0.75 | 0.78 | |
| Total | 100.00 | 100.00 | 100.00 | |
| % Conversion | — | 90.7 | 86.4 | 98.7 |
| % Selectivity | — | 100.0 | 86.5 | 98.9 |

Examples 70–73 demonstrate that high conversions are possible at a wide range of flow rates (WHSV) of from about 0.54 to about 4.14 grams of feed per gram of catalyst per hour using a continuous dehydrogenation procedure. As the flow rates increase the conversion decreases; however, the selectivity to 1,5- and 1,6-DMN increases. Example 74 and 75 demonstrate that even after many hours of liquid phase operation high conversion and selectivities are maintained at a reaction temperature of about 400° C. Noble metal catalysts in general require the addition of large amounts of hydrogen to maintain catalytic activity for prolonged periods. However, by employing reaction conditions in the dehydrogenation method of this invention such that a liquid reaction mixture was maintained, additional hydrogen was not required to maintain catalyst activity. In commercial operation, expensive hydrogen recycle equipment would not, therefore, be required. Examples 76 and 77 demonstrate that the continuous dehydrogenation reaction can be run in at least a two-pass process wherein the product stream from the first pass through the reactor, after the removal of hydrogen, is feed to a second fixed bed reactor. This type of operation can promote the dehydrogenation reaction by providing for the removal of hydrogen between reactors and thereby increasing the conversion and selectivity of the dehydrogenation reaction of this invention. By using this two-pass process conversion was increased from 90.7% for the first pass to 98.7% after the second pass, as demonstrated by a comparison of the data from Example 76 in Table 11 to the overall conversion reported in Table 11.

EXAMPLE 78

In Example 78, 32 parts by weight of crude 1,5-dimethyltetralin (1,5-DMT) and 0.96 parts by weight of UOP's LZ-Y72 catalyst were introduced into a reactor, and the contents of the reactor were heated in the first run to the desired reaction temperature of 182° C., and 5-o-tolyl-pentene-2 (OTP) was introduced into the reactor slowly over a 2-hour period in order to allow removal of the exothermal heat and maintenance of good temperature control. A total of 48 parts of 5-o-tolyl-pentene-2 was added. The pressure was adjusted so as to maintain the reactants at their boiling point in the liquid phase. When the cyclization reaction was substantially complete and at least 99 weight percent of the 5-o-tolyl-pentene-2 had reacted, the reactor pressure was reduced to 2–4 psia. and the dimethyltetralin components of the product mixture were removed by low pressure distillation. The higher boiling materials and catalyst remained in the reactor as residue from the first run.

In the second run, the procedure of the first run was repeated, except that the higher boiling residue from the previous run was used instead of the crude 1,5-DMT and no additional catalyst was introduced. In each of the third, fourth and fifth runs, the procedure of the second run was repeated. The overall combined composition of the feedstocks employed in the five runs is indicated in Table 12. The lower boiling products withdrawn as distillates in the five runs were combined, and the composition of this combination is also indicated in Table 12. The higher boiling product remaining in the reactor as residue from the fifth run was analyzed, and its composition is also reported in Table 12. This residue from the fifth run and distillation was then subjected to cracking under the same conditions and treatment employed in the fifth run, except that a reaction temperature of 250°–260° C. was employed and no 5-o-tolyl-pentene-2 was added. The cracked products boiling below the cracking temperature were removed by low pressure distillation as the "final distillate," and its composition is reported in Table 12. The higher boiling products remained in the reactor as the "final residue", and its composition is also reported in Table 12. The overall composition of the total of the distillates from the five runs and the final distillate from the fifth distillation residue is reported in Table 12 as the combined 6 Distillates.

The results of Example 78 illustrate clearly that the distillation overhead which contain the dimethyltetralins (DMTs) and serves as the feedstock for the subsequent dehydrogenation to form dimethylnaphthalenes (DMNs) contains no detectable heavies. Also, since the cyclization catalyst is not separated from the heavy distillation bottoms and is recycled to the cyclization step with this heavy fraction, there are no losses of catalyst due to filtration or other separation of the catalyst. The cracking step also reduces the total amount of unuseful distillation residue from 5.11 weight percent to 1.25 weight percent of the total product and therefore increases the absolute amount of useful DMTs and DMNs produced in the cyclization reaction.

analyzed. The solid catalyst and heavy products remaining in the reactor constituted approximately 25 weight percent of total cyclization product mixture. The heavy products and catalyst remaining in the reactor served as the heel for the next run, as described below.

In each of Examples 81–86, to the heel (including the catalyst) from the previous example, using the proce-

TABLE 12

| | Composition | | | | | |
|---|---|---|---|---|---|---|
| | | | | Products from Cracking and Distillation of 5th Distillation Residue | | |
| Components | Combined 5 Feedstocks | Combined 5 Distillates | 5th Distillation Residue | Final Distillate | Final Residue | Combined 6 Distillates |
| OTP | 88.59 | 1.37 | 0 | 0 | 0 | 1.3 |
| Saturated OTP | 0.56 | 4.10 | 0 | 6.60 | 0 | 4.2 |
| Unknown DMT | 0.16 | 1.29 | 0 | 5.10 | 0 | 1.4 |
| 1,6-DMT | 0.27 | 3.20 | 0.28 | 10.80 | 0 | 3.5 |
| 2,5-DMT | 0.06 | 1.40 | 0.26 | 8.6 | 0 | 1.7 |
| 1,5-DMT | 9.54 | 83.81 | 11.1 | 8.9 | 0 | 80.9 |
| 1,6-DMN | 0.03 | 0.41 | 0.36 | 3.3 | 0 | 0.5 |
| 1,5-DMN | 0.28 | 1.87 | 1.67 | 0.9 | 0 | 1.9 |
| Heavies | 0.51 | 0.06 | 83.5 | 1.00 | 100.0 | 0.1 |
| Other | 0.30 | 2.49 | 2.83 | 54.76 | 0 | 4.5 |
| Total useful DMTs and DMNs | 10.18 | 90.68 | 13.67 | 32.54 | 0 | 88.5 |
| Total | 100.00 | 100.00 | 100.00 | 100.00 | 100.00 | 100.00 |
| Percent of total product | — | 94.89 | 5.11 | 3.86 | 1.25 | 98.75 |

EXAMPLES 79–86

Each of Examples 79–86 was performed batchwise. In Example 79, 150 grams of 5-o-tolyl-pentene-2 and 1.80 grams of the particular solid cyclization catalysts employed were charged to a reactor equipped with a reflux condenser and distillation/collection head, and the reactor was evacuated to the desired reaction pressure. The reactor contents were then heated to the reaction temperature, at which point the reactor contents were at reflux. The pressure was controlled to maintain the reactants in the liquid phase. When at least 99 weight percent of the 5-o-tolyl-pentene-2 was convened, as indicated by gas chromatographic measurement, the reaction time was noted, and the temperature of the reactor contents was gradually reduced, and the pressure was gradually increased to atmospheric pressure. No product was distilled out of or removed from the reactor. When cooled, the reactor contents included the cyclization product mixture and solid catalyst employed, and a 1.8 gm sample of the product mixture was withdrawn for analysis.

In Example 80, the entire product mixture and catalyst from Example 79 was returned to the reactor as the heel for the next batch of 5-o-tolyl-pentene-2. Additional solid cyclization catalyst was added to this heel, and the reactor was heated under reduced pressure to obtain reflux at the desired reaction temperature in the liquid state. A portion of 5-o-tolyl-pentene-2 was then gradually added to the reaction mixture over a period of 2 hours to allow removal of the exothermic heat and maintenance of good temperature control. Unlike Example 79, at the end of the reaction time—that is, when at least 99 weight percent of the 5-o-tolyl-pentene-2 has reacted—as indicated by gas chromatographic analysis, the pressure is slowly reduced to 2.4 pounds per square inch absolute, and slowly the temperature was decreased to below the reaction temperature. The products that distilled were collected outside the reactor and dure of Example 80, a portion of 5-o-tolyl-pentene-2, but no additional solid catalyst was added, and the reactor contents were heated and maintained under vacuum to allow reflux. At the completion of the cyclization reaction, the reactor pressure was reduced further, and the lighter products were flash distilled, collected and analyzed, and the heavy products and catalyst remaining in the reactor were employed as the heel for the next run (Example), also as described for Example 80. The catalyst employed in Examples 79–86 was Conteka CBV 760.

The conditions employed and results from Examples 79–86 are presented in Tables 13–14.

EXAMPLES 87–94

Example 87 was performed using the same general procedure employed in Example 79 and the product mixture produced in Example 87 served as the heel for Example 88. Examples 88–94 were performed using the same general procedures of Examples 80–86. The catalyst employed in Examples 87–94 was UOP's LZ-Y72. The conditions employed in, and the results from, Examples 87–94 are presented in Tables 15–16.

The properties of the Conteka CBV 760 and LZ-Y72 catalysts used in Examples 79–86 and 87–94, respectively, are provided in Table 17. In the case of the Conteka catalyst (Tables 13–14), the relatively higher activity thereof allowed operation at 180° C. with short reaction times. In Examples 80–86, no catalyst deactivation was observed, so no increase in temperature or reaction time was necessary to complete the OTP conversion. The weight percent of useful products for the Examples 80–86 was in the range of about 94.8% to about 96.2%, and averaged 95.7%. The cumulative yield of components in the useful product was 81.9 parts per 100 parts of OTP (i.e. 90%).

In the case of the LZ-Y72 catalyst (Tables 15-16), the catalyst gradually deactivated with successive batch runs, however batch temperature increases or reaction time increases compensated for such catalyst deactivation. The weight percent useful product in each batch was in the range of about 90 to about 92.8 weight percent, based on total batch product. The average weight percent of useful product produced was 91.5%, Examples 88 through 94. The amount of undesired DMT isomer was in the range of about 1.07% to about 1.34%, and averages 1.2%. The yield in early runs was low since a heel of the product remained in the system. After seven full batches, the cumulative amount of useful product obtained was 84.8 parts/100 parts of OTP (i.e. 85%).

EXAMPLE 95

In Example 95, for the run on the first day of operation 8.83 grams of Conteka 760 catalyst and 440 grams of a liquid reaction medium were introduced into a 1000-milliliter stirred tank reactor which was maintained at the desired reaction temperature and which was fitted with the overhead distillation column connected to a vacuum system. The reactor pressure was reduced to 0.2 to 0.3 atmosphere in order to achieve reflux at the desired reaction temperature, and then liquid 5-0-tolyl-2-pentene (OTP) was passed continuously through the liquid reaction medium in the reactor, and reaction product passed continuously upward into the distillation column. The portion of the reaction product boiling below about 265° C. (at 1 atmosphere pressure) was continuously withdrawn as overhead from the distillation column, and the higher boiling fractions were either returned to the reactor as distillation bottoms or never vaporized or passed into the distillation column.

A run for a particular day was concluded by discontinuing the flow of OTP into the reactor, cooling the reactor contents to room temperature, raising the reactor pressure to one atmosphere while purging the reactor with nitrogen in order to eliminate oxygen. To begin the next day's run, the reactor was heated to the desired reaction temperature, reactor pressure was reduced to 0.2–0.3 atmosphere in order to bring the reactor contents to reflux and then liquid OTP was again passed into the reactor, and into the heavy liquid reaction product that boiled above 265° C. (at 1 atmosphere pressure) and that remained in the reactor from the previous day's run, but without the introduction of additional catalyst or liquid reaction medium.

The reaction condition employed and the results from Example 95 are presented in Table 18.

TABLE 13

| | Example 79 | Example 80 | Example 81 | Example 82 | Example 83 | Example 84 | Example 85 | Example 86 |
|---|---|---|---|---|---|---|---|---|
| Heal wt. (g) | — | 148.2 | 171.6 | 179.1 | 206.0 | 204.8 | 199.6 | 197.6 |
| Liquid Wt. (g) | — | 146.4 | 164.4 | 171.9 | 198.8 | 197.6 | 192.4 | 190.4 |
| Catalyst wt. (g) | — | 1.8 | 7.2 | 7.2 | 7.2 | 7.2 | 7.2 | 7.2 |
| OTP wt. (g) | 150 | 448 | 450 | 439 | 420 | 450 | 441 | 451 |
| Added catalyst wt. (g) | 1.8 | 5.4 | 0 | 0 | 0 | 0 | 0 | 0 |
| Total catalyst weight (g) | 1.8 | 7.2 | 7.2 | 7.2 | 7.2 | 7.2 | 7.2 | 7.2 |
| Reaction temperature (°C.) | 180 | 180 | 180 | 180 | 180 | 180 | 180 | 180–200 |
| Reaction pressure (psia) | 2–4 | 2–4 | 2–4 | 2–4 | 2–4 | 2–4 | 2–4 | 2–4 |
| Reaction time (hrs.) | 3 | <2 | <2 | <2 | <2 | <2 | <2 | <2 |
| Reduced pressure (psia) | — | 1–2 | 1–3 | 2–3 | 2–3 | 2–3 | 2–3 | 2–3 |
| Distilled product wt. (g) | 1.8* | 431.8 | 442.5 | 412.1 | 421.2 | 455.2 | 443.0 | 444.7 |
| Residual product wt. (g) | 148.2 | 164.4 | 171.9 | 198.8 | 197.6 | 192.4 | 190.4 | 186.7 |

*a 1.8 g sample of the undistilled total 148.2 g residual product reactor contents

TABLE 14

| | Composition of Distilled Product Removed From Reactor (Wt. %) | | | | | | | |
|---|---|---|---|---|---|---|---|---|
| | Example 79 | Example 80 | Example 81 | Example 82 | Example 83 | Example 84 | Example 85 | Example 86 |
| Components | | | | | | | | |
| OTP | 0.2 | 0.0 | 0.0 | 0.1 | 0.0 | 0.1 | 0.1 | 0.0 |
| saturated OTP | 1.9 | 3.1 | 2.0 | 2.0 | 2.2 | 1.8 | 2.1 | 2.2 |
| unknown DMT isomers | 0.5 | 0.5 | 0.4 | 0.4 | 0.4 | 0.4 | 0.4 | 0.5 |
| 2,6-, 2,7- and 1,7-DMT | 0.1 | 0.1 | 0.1 | 0.1 | 0.1 | 0.1 | 0.1 | 0.1 |
| 1,6-DMT | 0.5 | 0.5 | 0.7 | 0.7 | 0.8 | 0.7 | 0.7 | 1.0 |
| 2,8-DMT | 0.8 | 0.8 | 0.8 | 0.8 | 0.8 | 0.8 | 0.9 | 0.8 |
| 2,5-DMT | 0.1 | 0.2 | 0.3 | 0.3 | 0.4 | 0.3 | 0.3 | 0.4 |
| 1,5-DMT | 87.3 | 93.1 | 94.1 | 93.9 | 93.4 | 93.7 | 93.5 | 93.1 |
| 2,6-, 2,7-DMN | 0.0 | 0.0 | 0.0 | 0.0 | 0.0 | 0.0 | 0.0 | 0.0 |
| 1,7-DMN | 0.0 | 0.0 | 0.0 | 0.0 | 0.0 | 0.0 | 0.0 | 0.0 |
| 1,6-DMN | 0.0 | 0.0 | 0.0 | 0.0 | 0.1 | 0.1 | 0.1 | 0.1 |
| 1,5-DMN | 0.8 | 0.7 | 1.0 | 1.1 | 1.1 | 1.3 | 1.1 | 1.0 |
| 1,8-DMN | 0.0 | 0.0 | 0.0 | 0.0 | 0.0 | 0.0 | 0.0 | 0.0 |
| Heavies | 3.4 | 0.0 | 0.1 | 0.1 | 0.1 | 0.1 | 0.2 | 0.2 |
| Unknown | 2.5 | 0.2 | 0.2 | 0.2 | 0.2 | 0.2 | 0.2 | 0.2 |
| Total useful DMTs | 88.0 | 94.1 | 95.2 | 94.9 | 94.7 | 94.8 | 94.5 | 94.6 |
| Total useful DMNs | 0.8 | 0.7 | 1.0 | 1.1 | 1.1 | 1.3 | 1.1 | 1.0 |
| Total useful products | 88.8 | 94.8 | 96.2 | 96.0 | 95.8 | 96.1 | 95.6 | 95.6 |
| Total products | 100 | 100 | 100 | 100 | 100 | 100 | 100 | 100 |
| Parts of Distilled Products per 100 parts of OTP feedstock (including Ex 79) | | | | | | | | |

TABLE 14-continued

| | Composition of Distilled Product Removed From Reactor (Wt. %) | | | | | | | |
|---|---|---|---|---|---|---|---|---|
| | Example 79 | Example 80 | Example 81 | Example 82 | Example 83 | Example 84 | Example 85 | Example 86 |
| Total useful products | — | 68.7 | 79.8 | 82.8 | 85.7 | 87.9 | 89.2 | 89.9 |
| Total major by-products | | | | | | | | |
| Saturated OTP | — | 2.2 | 2.1 | 2.0 | 2.1 | 2.0 | 2.0 | 2.1 |
| 2,7-Triad DMTs | — | 0.7 | 0.7 | 0.8 | 0.8 | 0.8 | 0.8 | 0.8 |
| Unknown DMT isomers | — | 0.4 | 0.4 | 0.4 | 0.4 | 0.4 | 0.4 | 0.4 |
| Unknowns | — | 0.1 | 0.1 | 0.1 | 0.2 | 0.2 | 0.2 | 0.2 |
| Heavies | — | 0.0 | 0.0 | 0.1 | 0.1 | 0.1 | 0.1 | 0.1 |

*the composition of the undistilled total reaction product remaining in the reactor

TABLE 15

| | Example 87 | Example 88 | Example 89 | Example 90 | Example 91 | Example 92 | Example 93 | Example 94 |
|---|---|---|---|---|---|---|---|---|
| Heel wt. (g) | — | 149.0 | 156.7 | 142.5 | 194.6 | 181.6 | 187.6 | 202.3 |
| Liquid wt. (g) | — | 147.2 | 149.5 | 135.3 | 187.4 | 174.4 | 180.4 | 195.1 |
| Catalyst wt. (g) | — | 1.8 | 7.2 | 7.2 | 7.2 | 7.2 | 7.2 | 7.2 |
| OTP wt. (g) | 150 | 440 | 440 | 440 | 403 | 417 | 420.6 | 406.6 |
| Added catalyst wt. (g) | 1.8 | 5.4 | 0.0 | 0.0 | 0.0 | 0.0 | 0.0 | 0.0 |
| Total Catalyst weight (g) | 1.8 | 7.2 | 7.2 | 7.2 | 7.2 | 7.2 | 7.2 | 7.2 |
| Reaction temperature (°C.) | 190 | 190 | 200 | 216 | 237 | 238 | 238 | 238 |
| Reaction pressure (psia) | 4-5 | 4-5 | 5-6 | 10-12 | 14.7 | 14.7 | 14.7 | 14.7 |
| Reaction time (hrs.) | 4.5 | 4.0 | 7.0 | 8.0 | 2.8 | 2.8 | 2.8 | 2.8 |
| Reduced pressure (psia) | — | 1-2 | 1-2 | 1-2 | 1-2 | 1-2 | 1-2 | 1-2 |
| Distilled product wt. (g) | 2.8* | 437.7 | 454.2 | 387.9 | 415.6 | 411.4 | 405.6 | 391.4 |
| Residual product wt. (g) | 147.2 | 149.5 | 135.3 | 187.4 | 174.8 | 180.4 | 195.1 | 210.3 |

*a 2.8 g sample of the undistilled total 147.2 residual product reactor contents

TABLE 16

| | Composition of Distilled Products Removed from Reactor (wt. %) | | | | | | | |
|---|---|---|---|---|---|---|---|---|
| Components | Example 87* | Example 88 | Example 89 | Example 90 | Example 91 | Example 92 | Example 93 | Example 94 |
| o-xylene | 0.1 | 0.1 | 0.1 | 0.2 | 0.3 | 0.2 | 0.2 | 0.2 |
| OTP | 0.3 | 0.1 | 0.3 | 0.1 | 0.2 | 0.1 | 0.1 | 0.1 |
| saturated OTP | 2.5 | 4.4 | 2.8 | 3.9 | 5.0 | 4.9 | 4.7 | 4.7 |
| Unknown DMT isomers | 0.9 | 1.2 | 1.0 | 1.3 | 1.8 | 1.8 | 1.8 | 1.7 |
| 2,6-, 2,7-, 1,7-DMT | 0.2 | 0.2 | 0.2 | 0.3 | 0.5 | 0.4 | 0.4 | 0.4 |
| 1,6-DMT | 0.9 | 0.9 | 0.9 | 1.2 | 2.5 | 2.3 | 1.9 | 1.9 |
| 2,8-DMT | 0.8 | 0.9 | 0.9 | 0.8 | 0.8 | 0.8 | 0.9 | 0.9 |
| 2,5-DMT | 0.3 | 0.3 | 0.4 | 0.6 | 0.9 | 0.8 | 0.7 | 0.8 |
| 1,5-DMT | 85.8 | 90.0 | 89.8 | 89.0 | 84.6 | 85.3 | 86.1 | 86.4 |
| 2,6-, 2,7-DMN | 0.0 | 0.0 | 0.0 | 0.0 | 0.0 | 0.0 | 0.0 | 0.0 |
| 1,7-DMN | 0.0 | 0.0 | 0.0 | 0.0 | 0.0 | 0.0 | 0.0 | 0.0 |
| 1,6-DMN | 0.1 | 0.0 | 0.1 | 0.1 | 0.3 | 0.3 | 0.3 | 0.2 |
| 1,5-DMN | 1.3 | 1.1 | 1.6 | 1.6 | 2.2 | 2.2 | 2.2 | 2.0 |
| 1,8-DMN | 0.0 | 0.0 | 0.1 | 0.0 | 0.0 | 0.0 | 0.0 | 0.0 |
| Heavies | 4.6 | 0.0 | 0.1 | 0.0 | 0.0 | 0.0 | 0.1 | 0.0 |
| Unknown | 0.8 | 0.2 | 0.6 | 0.3 | 0.2 | 0.1 | 0.1 | 0.1 |
| Total useful DMTs | 86.9 | 91.2 | 91.1 | 90.7 | 88.1 | 87.5 | 88.7 | 89.0 |
| Total useful DMNs | 1.4 | 1.1 | 1.7 | 1.7 | 2.5 | 2.5 | 2.5 | 2.2 |
| Total useful products | 88.3 | 92.3 | 92.8 | 92.4 | 90.6 | 90.0 | 91.2 | 91.2 |
| Total products | 100 | 100 | 100 | 100 | 100 | 100 | 100 | 100 |
| Parts of Distilled Products per 100 parts of OTP feedstock (including Ex. 87) | | | | | | | | |
| Total useful products | — | 68.2 | 79.6 | 79.9 | 82.7 | 83.8 | 84.4 | 84.8 |
| Total Major by-products | | | | | | | | |
| Saturated OTP | — | 3.3 | 3.1 | 3.2 | 3.6 | 3.8 | 3.9 | 4.0 |
| 2,7-triad DMTs | — | 0.8 | 1.0 | 1.0 | 1.1 | 1.1 | 1.1 | 1.1 |
| Unknown DMT isomer | — | 0.9 | 0.9 | 1.0 | 1.1 | 1.1 | 1.1 | 1.1 |
| Unknown | — | 0.1 | 0.4 | 0.3 | 0.3 | 0.3 | 0.2 | 0.2 |
| Heavies | — | 0.0 | 0.0 | 0.0 | 0.0 | 0.0 | 0.0 | 0.0 |

*the composition of the undistilled total reaction product remaining in the reactor

TABLE 17

| | Catalyst Characteristics | | | |
|---|---|---|---|---|
| | Cell Size (Angstroms) | SiO2/Al2O3 Bulk Molar Ratio | Na2O Content (Wt. %) | Na2O/Al2O3 Bulk Molar Ratio |
| LZ-Y72 Conteka | 24.51 | 5.1 | 2.5 | 0.17 |
| CBV 760 | 24.20 | 42 | 0.05 | 0.05 |

TABLE 18

| | | Day No. | | | | | | | | |
|---|---|---|---|---|---|---|---|---|---|---|
| | Initial Reaction Medium | 1 | 2 | 3 | 4 | 5 | 6 | 7 | 8 | Final Reaction Medium |
| Feed Reate (g/hr) | | 233 | 233 | 233 | 233 | 233 | 233 | 233 | 233 | |
| Catalyst Charge (g) | | 8.83 | 8.83 | 8.83 | 8.83 | 8.83 | 8.83 | 8.83 | 8.83 | |
| Average Temperature (C.) | | 200 | 200 | 200 | 200 | 200 | 200 | 210 | 210 | |
| Average Pressure (psia) | | 4.4 | 4.0 | 3.7 | 3.6 | 3.6 | 3.6 | 4.3 | 4.3 | |
| Hours on Feed for the Day (hrs.) | | 5.8 | 7.7 | 9.6 | 11.6 | 7.6 | 11.8 | 7.7 | 11.7 | |
| WHSV (g OTP/g cut-hr) | | 26.4 | 26.3 | 26.3 | 25.8 | 26.6 | 25.8 | 26.3 | 26.0 | |
| Wt. of Feed into the Reactor (g) | | 1349 | 1788 | 2235 | 2682 | 1788 | 2682 | 1788 | 2682 | |
| Reactor Contents (g) | 440 | 432 | 403 | 401 | 431 | 470 | 494 | 502 | 512 | 512 |
| Cumulative Conditions - End of Day | | | | | | | | | | |
| Hours on catalyst | | 6.8 | 13.5 | 23.1 | 34.9 | 42.5 | 54.3 | 62.0 | 73.7 | |
| Wt. of Feed into Reactor[1] | | 1781 | 3569 | 5804 | 8486 | 10274 | 12956 | 14744 | 17426 | |
| Wt. Feed/Wt. Catalyst | | 152 | 354 | 607 | 911 | 1113 | 1417 | 1619 | 1923 | |
| Ovehead Product Removed | | 1359 | 3166 | 5403 | 8055 | 9804 | 12462 | 14242 | 16914 | |

| | | Composition | | | | | | | | |
|---|---|---|---|---|---|---|---|---|---|---|
| | Initial Reaction | Average Distillate for Day No. | | | | | | | | Final Reaction |
| Component | Medium | 1 | 2 | 3 | 4 | 5 | 6 | 7 | 8 | Medium |
| OTP | 1.7 | 0.1 | 0.2 | 0.4 | 0.6 | 0.7 | 0.9 | 1.0 | 0.9 | 0.0 |
| 2,6-Triad DMT's and DMN's | 92.8 | 93.9 | 94.9 | 94.8 | 94.6 | 94.5 | 94.3 | 93.7 | 93.8 | 58.9 |
| Sat'd. OTP | 3.0 | 3.3 | 2.5 | 2.5 | 2.4 | 2.4 | 2.4 | 2.8 | 2.8 | 0.8 |
| 2,7-Triad DMT's | 0.9 | 1.2 | 1.1 | 1.1 | 1.1 | 1.1 | 1.1 | 1.1 | 1.1 | 0.5 |
| Heavies | 0.2 | 0.0 | 0.1 | 0.2 | 0.2 | 0.3 | 0.3 | 0.3 | 0.3 | 39.3 |

| | Cumulative Yield of Distillate Component Based on Total Reactor Charge After Day No. | | | | | | | |
|---|---|---|---|---|---|---|---|---|
| Component | 1 | 2 | 3 | 4 | 5 | 6 | 7 | 8 |
| OTP | 0.1 | 0.2 | 0.3 | 0.6 | 0.7 | 0.8 | 0.9 | 0.9 |
| 2,6-Triad DMTs and DMNs | 71.1 | 84.2 | 88.2 | 89.8 | 90.2 | 90.7 | 90.5 | 91.1 |
| Sat'd OTP | 2.5 | 2.2 | 2.3 | 2.3 | 2.3 | 2.3 | 2.7 | 2.7 |
| 2,7-Triad DMTs | 0.9 | 1.0 | 1.0 | 1.0 | 1.0 | 1.0 | 1.1 | 1.1 |
| Heavies | 0.0 | 0.1 | 0.2 | 0.2 | 0.3 | 0.3 | 0.3 | 0.3 |

EXAMPLE 96

Following seven batch runs similar to those described in Examples 79–86, a residue remained in the reactor vessel. This residue consisted mainly of high molecular weight dimers. These dimers were cracked back to DMT by extended heating solely in the presence of the catalyst at relatively low pressure. The DMT, once thus formed, was flash distilled out of the reactor.

The residue contained 7.2 g of the Conteka catalyst which had previously been used for the seven cycles of DMT production from OTP. The conversion was carried out at 220° C. and 127 Torr (2.5 psia) for 2 hours. The heavy by-product dimers comprised 71% (138.6 g) of the heel composition. The balance of the heel composition was DMT and DMN isomers.

A distilled product (128 g) containing 92.1% (117.9 g) useful components was obtained. The residue in the reactor contained 26.7 wt % useful components and 66.5% heavy dimers. Thus, 67.8 wt % of the heavies in the residue were converted to useful product with a selectivity of 88 wt %. This procedure is, in practice, an extension of the normal flash distillation procedure and only requires additional reaction time.

The results of this cracking procedure are shown in Table 19, below.

TABLE 19

| | Total | Useful Product | Undesired DMT Isomers | Heavies | Other |
|---|---|---|---|---|---|
| Feedstock | | | | | |
| Grams | 195 | 53.2 | 0.5 | 138.6 | 2.7 |
| Wt % | 100 | 27.3 | 0.3 | 71.1 | 1.4 |
| Product-Distilled | | | | | |
| Grams | 128 | 117.9 | 2.2 | 0.2 | 7.8 |
| Wt % | 65.6 | 92.1 | 1.7 | 0.1 | 6.1 |
| Product-Residue | | | | | |
| Grams | 67 | 17.9 | 0.4 | 44.6 | 4.2 |

TABLE 19-continued

|  | Total | Useful Product | Undesired DMT Isomers | Heavies | Other |
|---|---|---|---|---|---|
| Wt % | 34.4 | 26.7 | 0.5 | 66.5 | 6.3 |
| Total Product Wt. | 195 | 135.8 | 2.5 | 44.7 | 12.0 |

EXAMPLE 97

A batch conversion of OTP was conducted with a fresh sample of the Conteka catalyst and using a catalyst loading as employed in the procedure of Examples 79–86. Specifically, the present process procedure employed 10.2 g of previously prepared dimethyltetrahydronaphthalene, 94.4 g of OTP, and 0.32 g of the Conteka catalyst. The temperature was 190° C., and the pressure was 203 Torr (3.9 psia). A complete conversion of OTP was observed after 2 hours with 94.9% selectivity to useful product. After 18 hours, the conversion of OTP was still 100% with selectivity to useful product being 94.1%.

Following complete conversion of the OTP in two hours, the reactor was allowed to reflux at 19° C. for an additional 16 hours to simulate a very slow flashing step. The results are shown in Table 20 below. These results indicate that over a period of 16 hours the loss of useful products was only 0.6%. No increase in the amount of undesired DMT isomers was observed. These results show the low isomerization activity of the catalyst after cyclization.

TABLE 20

| Temp. °C. | Reaction Time (Hr) | Wt. % OPT | Wt % Useful In Product | Wt. % DMT Isom |
|---|---|---|---|---|
| Feed | 0 | 74 | 24.6 | 0.2 |
| 190 | 2 | 0 | 94.8 | 0.8 |
| 190 | 18 | 0 | 94.2 | 0.7 |

EXAMPLES 98–103

Batch runs were made in a manner similar to that employed in Examples 79–86 employing a previously used catalyst. The catalyst was also used for Example 96. Results are shown in Table 21, below. Temperature variations were made to observe the range of operability of the catalyst.

Example 98 was run under the same conditions as Examples 79 through 86 and demonstrates that the cracking of heavy by-products (Example 96, Table 19) was not detrimental to catalyst activity. Example 99 indicates that an increase in temperature to 190° C. is not detrimental to catalyst performance. In Example 100, the operation at 160° C. resulted in lower reaction rates. The presence of a small amount of water in the distillate of Example 100 indicated some catalyst poisoning. In Example 101, the temperature of the catalyst was increased to accelerate the reaction and to drive off water from the previous batch. In Example 102, the catalyst activity was noted to be lower than fresh catalyst, but still relatively high, yielding high conversion in 5.5 hours at 180° C. Finally, Example 103 was conducted at a higher temperature and demonstrates that even at such conditions selectivity and high yields could be obtained. For an entire series of 13 batch runs, the total OTP convened by the Conteka catalyst was 812 grams per gram of catalyst.

TABLE 21

| Example | Temp. C. | Reaction Time (Hr) | Feedstock Residue (Grams) | G OTP | Dist. Prod Grams | Wt. % OTP In Prod. | Wt. % Useful In Prod. | DMT Isom |
|---|---|---|---|---|---|---|---|---|
| 98 | 180 | 2.5 | 71.6 | 450.0 | 445.0 | 0.0 | 95.3 | 1.0 |
| 99 | 190 | 2.5 | 82.5 | 449.9 | 439.0 | 0.0 | 95.2 | 1.0 |
| 100 | 160 | 12.3 | 84.3 | 433.7 | 431.9 | 18.5 | 71.7 | 0.7 |
| 101 | 170–246 | 9.0 | 83.4 | 449.9 | 450.2 | 0.1 | 92.3 | 1.1 |
| 102 | 180 | 5.5 | 83.2 | 446.3 | 446 4 | 0.5 | 92.0 | 1.1 |
| 103 | 246 | 2.5 | 70.6 | 449.9 | 462.5 | 0.0 | 92.1 | 1.2 |

EXAMPLE 104

OTP was continuously fed to a stirred tank reactor equipped with an overhead condenser and maintained at reflux temperature for the reactor contents. The reflux temperature was modulated by adjusting the system pressure.

The product (DMT) was constantly removed from the overhead as a distillate. The heavy byproducts were retained in the reactor where they ultimately reached an equilibrium concentration, preventing further heavy formation.

The data presented in Table 22, below, illustrate 6 days of operation. The initial catalyst charge was a "low activity" sample of the Conteka 760 catalyst which required a reaction temperature of about 210° C. in the batch mode. After making 5 batch runs with this low activity catalyst, the hydrocarbon product from the 5th batch run was used as the reaction medium for the continuous cyclization. On the first day of operation (first column), the distillate contained 94% useful components (2,6-Triad DMT+DMN, without the xylene impurity present in the feed) and only 1% of the sum of OTP and an intermediate convertible to product. During the first day of operation, the heavies in the reactor increased such that the overall yield for the first day (noted at the bottom of the table) was only 81.5% of the 2,6-triad. On Days 2–6 the distillate quality was similar to the first day. However, the heavy formation in the reactor decreased, and on Day 3, addition of fresh catalyst actually yielded a net loss of heavies in the system (negative yield).

The overall results for the continuous run after 6 days (55 hours) are presented in the far right column of Table 22. The average distillate contained 93.3% useful components (xylene-free basis) and the overall yield of the 2,6-triad DMT+DMNs was 92.5%.

TABLE 22
CONTINUOUS CYCLIZATION IN A STIRRED TANK REACTOR

| | Day 1 | Day 2 | Day 3 | Day 4 | Day 5 | Day 6 | For Overall Run |
|---|---|---|---|---|---|---|---|
| Feed G/Hr (Approx.) | 4 | 4 | 4 | 4 | 4 | 4 | |
| Type Catalyst (Conteka CBV 760) | Used for 5 Batches Low Activity | | Add 3.5 G Fresh High Activity | | | | |
| G Low Activity Cat. | 7.1 | 7.1 | 7.1 | 7.1 | 7.1 | 7.1 | 7.1 |
| G High Activity Cat. | 0 | 0 | 3.5 | 3.5 | 3.5 | 3.5 | 3.5 |
| wt.-% Cat. in Reactor (Total) | 1.2 | 1.2 | 2 | 2 | 2 | 2 | 2 |
| Ave. Temp., °C. | 218 | 238 | 225 | 225 | 240** | 230–240 | 218–240 |
| Ave. Press, psia | 6.4 | 6.2 | 6.4 | 6.4 | 9–12 | 7–11 | 6–12 |
| Hrs. on Feed for Day | 6.7 | 13 | 10.1 | 8.1 | 10 | 7.1 | 55 |
| G of Feed into Reactor | 1259 | 2902 | 2235 | 1981 | 1670 | 1861 | 11916 |
| Cumulative-End of Day | | | | | | | |
| Hr. on Low Act. Cat. | 37 | 50 | 60 | 68 | 78 | 85 | 85 |
| Hrs. On Hi Act. Cat. | — | — | 10 | 18 | 28 | 35 | 35 |
| G Feed into Reactor | 3644 | 6546 | 8781 | 10762 | 12432 | 14301 | 14301 |
| G Feed/G Cat. | 513 | 922 | 828 | 1015 | 1173 | 1349 | 1349 |
| Average Product (Distillate) Composition for Each Day - Weight Percent | | | | | | | |
| o-Xylene | 1.5 | 1.1 | 1.1 | 1.1 | 0.8 | 0.9 | 1.1 |
| SAT OTP | 1.7 | 1.5 | 2.4 | 2.2 | 2.9 | 2.1 | 2.1 |
| OTP + Intermed. | 1.0 | 3.2 | 0.9 | 1.1 | 0.5 | 0.8 | 1.4 |
| 2,6-Triad DMT + DMN* | 92.6 | 90.7 | 92.9 | 93.0 | 91.7 | 93.4 | 92.3 |
| 2,7-Triad DMT | 0.9 | 0.9 | 0.8 | 0.8 | 0.9 | 0.9 | 0.9 |
| Heavy | 0.0 | 0.0 | 0.1 | 0.2 | 0.6 | 0.0 | 0.1 |
| Other | 2.3 | 2.5 | 1.8 | 1.5 | 2.6 | 1.8 | 2.1 |
| TOTAL | 100.0 | 100.0 | 100.0 | 100.0 | 100.0 | 100.0 | 100.0 |
| *2,6-Triad w/o Xylene | 94.0 | 91.7 | 93.9 | 94.0 | 92.5 | 94.3 | 93.3 |
| Average Daily Yields - Including Change in Reactor Composition and Quantiy G Component/100 G Tolylpentenes | | | | | | | |
| Sat. OTP | 1.5 | 1.5 | 2.7 | 2.2 | 3.0 | 2.0 | 2.1 |
| OTP | 0.9 | 3.2 | 1.0 | 1.1 | 0.5 | 0.8 | 1.4 |
| 2,6-Triad DMT + DMN | 81.5 | 89.1 | 102.7 | 93.2 | 96.0 | 88.5 | 92.5 |
| 2,7-Triad DMT | 0.8 | 0.9 | 0.9 | 0.8 | 0.9 | 0.9 | 0.9 |
| Heavy | 13.3 | 2.8 | −9.3 | 1.1 | =3.2 | 6.2 | 1.0 |
| Other | 2.0 | 2.5 | 1.9 | 1.5 | 2.7 | 1.7 | 2.1 |
| TOTAL | 100.0 | 100.0 | 100.0 | 100.0 | 100.0 | 100.0 | 100.0 |

Although the present invention has been described and illustrated based on the presently available information and embodiments, it is to be understood that modifications and variations are within the spirit and scope of the invention, as those skilled in the art will readily appreciate and that such are within the purview and scope of the appended claims.

Having described the invention, what is claimed is:

1. A method for preparing one or more dimethyltetralins from 5-(o- m-, or p-tolyl)-pent-1- or -2-ene or 5-phenyl-hex-1- or -2-ene as the first feedstock, comprising: contacting the first feedstock in liquid form with a solid cyclization catalyst comprising an ultra-stable thermally stabilized or dealuminated crystalline aluminosilicate molecular sieve Y-zeolite that has a silica-to-alumina molar ratio of from about 3:1 to about 200:1, pore windows provided by twelve-membered rings containing oxygen and a unit cell size of from 24.0 to about 24.7 Angstroms, and that contains from about 0.01 up to about 3.5 weight percent of sodium, calculated as elemental sodium, and based on the weight of the zeolite and that is substantially free of adsorbed water, and at an elevated temperature and at a pressure that is sufficiently high to maintain the first feedstock substantially in the liquid phase, to thereby cyclize the first feedstock to form a first liquid product comprising one or more dimethyltetralins, wherein water is at a concentration in the first feedstock of from zero up to less than about 0.5 weight percent, based on the weight of the feedstock, wherein (1) when the first feedstock comprises 5-(o-tolyl)-pent-1 or -2-ene, at least 80 weight percent of the dimethyltetralin product formed is comprised by 1,5-, 1,6-, 2,5- or 2,6-dimethyltetralin or a mixture thereof, (2) when the first feedstock comprises 5-(m-tolyl)-pent-1 or -2-ene, at least 80 weight percent of the dimethyltetralin product formed is comprised by 1,5-, 1,6-, 1,7-, 1,8-, 2,5-, 2,6-, 2,7- or 2,8-dimethyltetralin or a mixture thereof, (3) when the first feedstock comprises 5-(p-tolyl)-pent-1 or -2-ene, at least 80 weight percent of the dimethyltetralin product formed is comprised by 1,7-, 1,8-, 2,7- or 2,8-dimethyltetralin or a mixture thereof, or (4) when the first feedstock comprises 5-phenyl-hex-1- or -2-ene, at least 80 weight percent of the dimethyltetralin product formed is comprised of 1,3-, 1,4-, 2,3-, 5,7-, 5,8- or 6,7-dimethyltetralin or a mixture thereof.

2. The method of claim 1 wherein the first feedstock comprises 5-(o-tolyl)-pent-1- or -2-ene and at least 80 weight percent of the dimethyltetralin product formed comprises 1,5-, 1,6-, 2,5- or 2,6-dimethyltetralin or a mixture thereof.

3. The method of claim 1 wherein the first feedstock comprises 5-(m-tolyl)-pent-1- or -2-ene and at least 80 weight percent of the dimethyltetralin product formed comprises 1,5-, 1,6-, 1,7-, 1,8-, 2,5-, 2,6-, 2,7-, or 2,8-dimethyltetralin or a mixture thereof.

4. The method of claim 1 wherein the first feedstock comprises 5-(p-tolyl)-pent-1- or -2-ene and at least 80 weight percent of the dimethyltetralin product formed comprises 1,7-, 1,8-, 2,7- or 2,8-dimethyltetralin or a mixture thereof.

5. The method of claim 1 wherein the first feedstock comprises 5-phenyl-hex-1- or -2-ene and at least 80 weight percent of the dimethyltetralin product formed comprises 1,3-, 1,4-, 2,3-, 5,7-, 5,8-, or 6,7-dimethyltetralin or a mixture thereof.

6. The method of claim 1 wherein the cyclization is performed at a temperature in the range of from about 120° C. to about 400° C.

7. The method of claim 1 wherein the cyclization is performed on a batch basis.

8. The method of claim 1 wherein the cyclization is performed on a continuous basis with a space velocity of, or on a batch basis with an effective space velocity of, from about 0.01 to about 100 parts of feedstock per part of the zeolite component of the cyclization catalyst by weight per hour.

9. The method of claim 1 wherein said solid cyclization catalyst comprises an acidic, ultrastable Y-zeolite having a unit cell size in the range of about 24.2 to about 24.7 Angstroms, a silica-to-alumina bulk molar ratio in the range of about 4:1 to about 10:1, and a sodium content of about 0.05 to about 3.5 weight percent, calculated as elemental sodium.

10. The method of claim 1 wherein said solid cyclization catalyst comprises a relatively low acidity ultrastable Y-zeolite having a unit cell size of no more than about 24.3 Angstroms, a silica-to-alumina bulk molar ratio of at least about 12, and a sodium content of less than about 0.4 weight percent, based on the weight of the zeolite and calculated as elemental sodium.

11. A method for preparing one or more dimethyltetralins from 5-(o-, m-, or p-tolyl)-pent-1- or -2-ene or 5-phenyl-hex-1- or -2-ene, comprising:

(a) contacting a feedstock comprising 5-(o,m-, or p-tolyl)-pent-1- or 2-ene or 5-phenyl-hex-1- or -2-ene in liquid form with a solid cyclization catalyst comprising an acidic ultrastable, thermally stabilized or dealuminated crystalline aluminosilicate molecular sieve Y-zeolite that is substantially free of absorbed water, and at an elevated temperature and at a pressure that is sufficiently high to maintain the feedstock substantially in the liquid phase, to thereby cyclize the first feedstock to form a liquid product comprising one or more dimethyltetralins, wherein water is at a concentration in the first feedstock of from zero up to less than about 0.5 weight percent, based on the weight of the feedstock, wherein (1) when the feedstock comprises 5-(o-tolyl)-pent-1- or -2-ene, at least 80 weight percent of the dimethyltetralin product formed is comprised of 1,5-, 1,6-, 2,5- or 2,6-dimethyltetralin or a mixture thereof, (2) when the feedstock comprises 5-(m-tolyl)-pent- 1- or -2-ene, at least 80 weight percent of the dimethyltetralin product formed is comprised of 1,5-, 1,6-, 1,7-, 1,8-, 2,5-, 2,6-, 2,7- or 2,8-dimethyltetralin or a mixture thereof, (3) when the feedstock comprises 5-(p-tolyl)-pent-1- or -2-ene, at least 80 weight percent of the dimethyltetralin product formed is comprised of 1,7-, 1,8-, 2,7- or 2,8-dimethyltetralin or a mixture thereof, or (4) when the feedstock comprises 5-phenyl-hex-1- or -2-ene, at least 80 weight percent of the dimethyltetralin product formed is comprised of 1,3-, 1,4-, 2,3-, 5,7-, 5,8- or 6,7-dimethyltetralin or a mixture thereof;

(b) separating the resulting cyclization product mixture by distillation at reduced pressure into a lighter, lower boiling fraction that comprises the dimethyltetralin product and a heavier, higher boiling fraction boiling above the boiling point of the dimethyltetralin product, and withdrawing the resulting lighter fraction as distillation overhead; and (c) combining the resulting heavier fraction with a fresh supply of the tolyl-pentene(s) or phenyl-hexene(s) employed in step (a), cyclizing the resulting mixture under the cyclization conditions employed in step (a), and separating the resulting cyclization product mixture under the distillation conditions employed in step (b).

12. The method of claim 11 wherein in step (b), the heavier fraction boils above about 240° C. at 1 atmosphere.

13. The method of claim 11 wherein, when steps (a)–(c) are performed on a batch basis, from about 0.01 to about 2 parts by weight of the heavier fraction from step (b) are combined in step (c) per part by weight of fresh supply of tolyl-pentene(s) or phenyl-hexene(s).

14. The method of claim 13 wherein, from about 0.05 to about 0.35 parts by weight of the heavier fraction from step (b) are combined in step (c) per part by weight of the fresh supply of tolyl-pentene(s) or phenyl-hexene(s).

15. The method of claim 11 wherein, when steps (a)–(c) are performed continuously, from about 0.2 to about 20 parts by weight of the heavier fraction from step (b) are combined in step (c) per part by weight of the fresh supply of tolyl-pentene(s) or phenyl-hexene(s).

16. The method of claim 15, wherein from about 1 to about 5 parts by weight of the heavier fraction from step (b) are combined in step (c) per part by weight of the fresh supply of tolyl-pentene(s) or phenyl-hexene(s).

17. The method of claim 11 wherein, when steps (a)–(c) are performed on a batch basis, the sequence of steps (b) and (c) is repeated from one to about 100 times.

18. The method of claim 11 wherein, when steps (a)–(c) are performed continuously, a portion of the catalyst is periodically withdrawn and replaced with fresh catalyst.

19. The method of claim 11 wherein the following additional steps are performed:

(d) cracking the resulting separated heavier fraction from step (c) in the presence of a solid cracking catalyst at a cracking temperature in the range of from about 120° C. to about 450° C., which temperature is at least 10° C. above the temperature employed for the cyclization of step (c) and at a pressure that is sufficiently high to maintain the heavier fraction being cracked substantially in the liquid phase; and (e) separating the resulting cracking product mixture by distillation at reduced pressure into a lighter, lower boiling fraction that comprises the dimethyltetralin product and a heavier, higher boiling fraction that boils above the boiling point of the dimethyltetralin product.

20. The method of claim 19 wherein the heavier fraction in step (e) boils above about 240° C. at one atmosphere.

21. The method of claim 19 wherein the cracking temperature in step (d) is in the range of from about 180° C. to about 330° C.

22. The method of claim 19 wherein the cracking temperature in step (d) is at least 30° C. above the cyclization temperature in step (c).

23. The method of claim 19 wherein the cracking catalyst comprises the catalyst employed for cyclization in steps (a) and (c).

24. The method of claim 19 wherein in step (e) the heavier fraction boils above about 240° C.

25. The method of claim 11 wherein said solid cyclization catalyst comprises an acidic, ultrastable Y-zeolite having a unit cell size in the range of about 24.2 to about 24.7 Angstroms, a silica-to-alumina bulk molar ratio in the range of about 4:1 to about 10:1, and a sodium content of about 0.05 to about 3.5 weight percent, calculated as elemental sodium.

26. The method of claim 11 wherein said solid cyclization catalyst comprises a relatively low acidity ultrastable Y-zeolite having a unit cell size of no more than about 24.3 Angstroms, a silica-alumina bulk molar ratio of at least about 12, and a sodium content of less than about 0.4 weight percent, based on the weight of the zeolite and calculated as elemental sodium.

27. A method for preparing one or more of dimethylnaphthalenes comprising contacting the first liquid product from claim 1 as a second feedstock in liquid form with a solid dehydrogenation catalyst in a reaction vessel at an elevated temperature and at a pressure that is sufficiently high to maintain the second feedstock substantially in the liquid phase, to thereby effect conversion of the aforesaid first liquid product in an equilibrium dehydrogenation reaction to form hydrogen and a second liquid product comprising said one or more dimethylnaphthalenes, and removing a substantial portion of the hydrogen being formed in the dehydrogenation reaction from the reaction vessel to thereby shift the aforesaid equilibrium toward the formation of the aforesaid one or more dimethylnaphthalenes, wherein (a) when 1,5-, 1,6-, 2,5-, or 2,6-dimethyltetralin or a mixture thereof comprises at least 80 weight percent of the dimethyltetralin product formed in (1) of claim 1 and present in the second feedstock, at least 80 weight percent of the dimethylnaphthalene product in the second liquid product is comprised of 1,5-, 1,6- or 2,6-dimethylnaphthalene or a mixture thereof, or (b) when 1,5-, 1,6-, 1,7-, 1,8-, 2,5-, 2,6-, 2,7- or 2,8-dimethyltetralin or a mixture thereof comprises at least 80 weight percent of the dimethyltetralin product formed in (2) of claim 1 and present in the second feedstock, at least 80 weight percent of the dimethylnaphthalene product in the second liquid product is comprised of 1,5-, 1,6-, 1,7-, 1,8-, 2,6- or 2,7-dimethylnaphthalene or a mixture thereof or (c) when 1,7-, 1,8-, 2,7- or 2,8-dimethyltetralin or a mixture thereof comprises at least 80 weight percent of the dimethyltetralin product formed in (3) of claim 1 and present in the second feedstock, at least 80 weight percent of the dimethylnaphthalene product in the second liquid product is comprised of 1,7-, 1,8-, or 2,7-dimethylnaphthalene or a mixture thereof or (d) when 1,3-, 1,4-, 2,3-, 5,7-, 5,8- or 6,7-dimethyltetralin or a mixture thereof comprises at least 80 weight percent of the dimethyltetralin product formed in (4) of claim 1 and present in the second feedstock, at least 80 weight percent of the dimethylnaphthalene product in the second liquid product is comprised of 1,3-, 1,4- or 2,3-dimethylnaphthalene or a mixture thereof.

28. A method for isomerizing at least 20 weight percent of the total of (1) the 1,5-, and 1,6-dimethylnaphthalenes in the second liquid product in (a) of claim 27 to 2,6-dimethylnaphthalene, (2) the 1,5-, 1,6-, 1,7-, and 1,8-dimethylnaphthalenes in the aforesaid second liquid product in (b) of claim 27 to 2,7-dimethylnaphthalene and 2,6-dimethylnaphthalene, (3) the 1,7- and 1,8-dimethylnaphthalene in the aforesaid second liquid product in (c) of claim 27 to 2,7-dimethylnaphthalene, or (4) the 1,3- and 1,4-dimethylnaphthalene in the aforesaid second liquid product in (d) of claim 27 to 2,3-dimethylnaphthalene, comprising: contacting the aforesaid second liquid product in liquid form with a solid isomerization catalyst comprising either beta zeolite or an acidic ultrastable crystalline Y-zeolite having a silica-to-alumina molar ratio of from about 4:1 to about 10:1, having pore windows provided by twelve-membered rings containing oxygen and a unit cell size of from about 24.2 to about 24.7 angstroms, and at an elevated temperature and at a pressure that is sufficiently high to maintain the isomerization feedstock substantially in the liquid phase.

* * * * *

UNITED STATES PATENT AND TRADEMARK OFFICE
CERTIFICATE OF CORRECTION

PATENT NO. : 5,401,892                                Page 1 of 3
DATED       : March 28, 1995
INVENTOR(S) : David L. Sikkenga, et al It is certified that error appears in the above-indentified patent and that said Letters Patent is hereby corrected as shown below:

| Col. | Line | |
|---|---|---|
| Item [54] and col. 3 | 2-3 | in the title, patent reads "CYCLIZING AN ORTHOTOLYLPENTENE PHENYLHEXENE" patent should read --CYCLIZING AN ORTHOTOLYLPENTENE OR PHENYLHEXENE-- |
| 8 | 22 | "the use of less severs conditions" should read --the use of less severe conditions-- |
| 11 | 34-35 | "the dimethyltetralin(s) therein are convened" should read --the dimethyltetralin(s) therein are converted-- |
| 22 | 60 | in "TABLE 4" under column "Ex. 33" patent reads "YZ-Y82$^1$" patent should read --LZ-Y82$^1$-- |
| 31 | 15 | in "TABLE 10" underneath the column "Products" patent reads "2-Meothylnaphthalene" patent should read --2-Methylnaphthalene-- |

UNITED STATES PATENT AND TRADEMARK OFFICE
CERTIFICATE OF CORRECTION

PATENT NO. : 5,401,892  
DATED : March 28, 1995  
INVENTOR(S) : David L. Sikkenga, et al Page 2 of 3

It is certified that error appears in the above-indentified patent and that said Letters Patent is hereby corrected as shown below:

| Col. | Line | |
|---|---|---|
| 33 | 42-43 | "the 5-o-tolyl-pentene-2 was convened," should read --the 5-o-tolyl-pentene-2 was converted,-- |
| 35 | 31 | in "TABLE 13" in the first column patent reads "Heal wt. (g)" patent should read --Heel wt. (g)-- |
| 37 | 22 | in "TABLE 15" in the first column patent reads "Addod catalyst wt. (g)" patent should read --Added catalyst wt. (g)-- |
| 39 | 28 | in "TABLE 18" underneath column "1" patent reads "6.8" patent should read --5.8-- |
| 42 | 14 | "total OTP convened" should read --total OTP converted-- |
| 42 | 21-22 | in "TABLE 21" the last column entitled "DMT Isom" should read --Wt. % DMT Isom-- |

UNITED STATES PATENT AND TRADEMARK OFFICE
CERTIFICATE OF CORRECTION

PATENT NO. : 5,401,892
DATED : March 28, 1995
INVENTOR(S) : David L. Sikkenga, et al It is certified that error appears in the above-indentified patent and that said Letters Patent is hereby corrected as shown below:

| Col. | Line | |
|---|---|---|
| 44 | 32 | in "TABLE 22" underneath column "5" patent reads "=3.2" patent should read -- -3.2 -- |

Signed and Sealed this

Eleventh Day of July, 1995

Attest:

BRUCE LEHMAN

Attesting Officer

Commissioner of Patents and Trademarks